(12) United States Patent
Yu et al.

(10) Patent No.: US 11,866,415 B2
(45) Date of Patent: Jan. 9, 2024

(54) LIGAND-ENABLED β-C(SP³)-H LACTONIZATION FOR β-C—H FUNCTIONALIZATIONS

(71) Applicant: THE SCRIPPS RESEARCH INSTITUTE, La Jolla, CA (US)

(72) Inventors: Jin-quan Yu, San Diego, CA (US); Zhe Zhuang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 96 days.

(21) Appl. No.: 17/615,509

(22) PCT Filed: May 29, 2020

(86) PCT No.: PCT/US2020/070100
§ 371 (c)(1),
(2) Date: Nov. 30, 2021

(87) PCT Pub. No.: WO2020/243754
PCT Pub. Date: Dec. 3, 2020

(65) Prior Publication Data
US 2022/0306595 A1    Sep. 29, 2022

Related U.S. Application Data

(60) Provisional application No. 62/854,807, filed on May 30, 2019.

(51) Int. Cl.
| | | |
|---|---|---|
| *C07D 305/12* | (2006.01) | |
| *C07D 405/06* | (2006.01) | |
| *C07D 407/04* | (2006.01) | |
| *C07D 407/06* | (2006.01) | |
| *C07F 9/655* | (2006.01) | |

(52) U.S. Cl.
CPC ......... *C07D 305/12* (2013.01); *C07D 405/06* (2013.01); *C07D 407/04* (2013.01); *C07D 407/06* (2013.01); *C07F 9/6551* (2013.01)

(58) Field of Classification Search
CPC .................................................. C07D 305/12
See application file for complete search history.

(56) References Cited

U.S. PATENT DOCUMENTS 4,221,809 A * 9/1980 Buendia ............... C07D 309/12
                                                                514/456

* cited by examiner

*Primary Examiner* — Golam M Shameem
(74) *Attorney, Agent, or Firm* — Jennifer Kisko; Thomas Fitting

(57) ABSTRACT

Provided herein is a method of forming a beta-lactone from a carboxylic acid having a beta-carbon with a hydrogen atom disposed thereon. The method comprises contacting a carboxylic acid of formula (1) as described herein with an effective amount of a palladium(II) catalyst, an effective amount of an N-protected aminoacid ligand, and t-butylhydroperoxide in a solvent comprising hexafluoroisopropanol (HFIP), at about 60° C. to provide a beta-lactone of formula (2) as described herein.

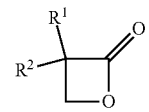

(2)

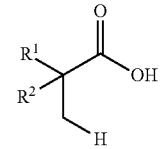

(1)

7 Claims, 4 Drawing Sheets

A

B

C

LIGAND-ENABLED β-C(SP³)-H LACTONIZATION FOR β-C—H FUNCTIONALIZATIONS

CLAIM OF PRIORITY

The present application claims the benefit of priority to U.S. Provisional Application No. 62/854,807 filed on May 30, 2019, which application is incorporated herein as if fully set forth.

STATEMENT OF GOVERNMENT SUPPORT

This invention was made with government support under grant number GM084019 awarded by the National Institutes of Health. The government has certain rights in the invention.

BACKGROUND

The past two decades have witnessed rapid development of carbon-carbon (C—C) and carbon-heteroatom (C—Y) bond-forming reactions based on palladation of C(sp³)-H bonds (1-3). Alkyl carboxylic acids are ubiquitous, inexpensive reagents in organic chemistry available in a great diversity of substitution patterns: as such, they are highly desirable substrates for C—H activation reactions (4-5). To access a wide range of β-substituted aliphatic acids, diverse transformations have to be developed to install different carbon fragments or functional groups. Challenges of developing C—H activation reactions includes extensive catalyst design and directing group optimizations for each transformation, and the often limited scope of transformations due to incompatibility of certain reaction partners. For example, for C—C bond formations, alkylation reactions are limited to primary alkyl iodide or alkyl boron coupling partners (6-8), olefination reactions are limited to electron-deficient olefins (9, 10), and heteroarylation reactions are highly limited in scope (11-14) despite the design of various directing groups. Further, most of these reactions are incompatible with free aliphatic acids without exogenous directing groups.

SUMMARY

In an embodiment, the present disclosure provides a method of forming a beta-lactone of formula (2):

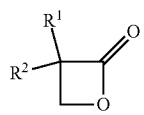
(2)

from a carboxylic acid having a beta-carbon with a hydrogen atom disposed thereon. The method comprises contacting a carboxylic acid of formula (1):

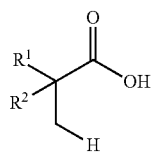
(1)

$R^1$ and $R^2$ are each independently H or alkyl, provided that at least one of $R^1$ and $R^2$ is alkyl. In some embodiments, the alkyl is unsubstituted or, in other embodiments, is substituted with halo, oxo, dialkylphosphono, cycloalkyl, alkoxy, aryloxy, benzyloxy, heterocyclyl, aryl, or heteroaryl.

The contacting occurs in the presence of an effective amount of a palladium(II) catalyst, an effective amount of an N-protected aminoacid ligand, and t-butylhydroperoxide in a solvent comprising hexafluoroisopropanol (HFIP), at about 60° C., to provide the beta-lactone of formula (2).

In an additional embodiment, the method further comprises contacting the beta-lactone of formula (2):

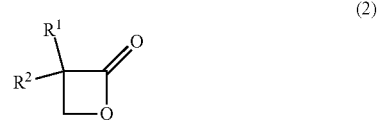
(2)

with a nucleophile (Nu) to provide a beta-functionalized carboxylic acid of formula (3):

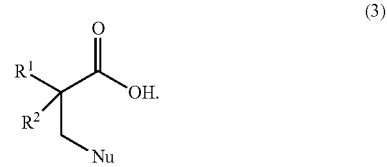
(3)

Nu is selected from the group consisting of C(sp³), C(sp²), CN, $N_3$, 2-nitrophenylsulfonamido, OH, F, Br, and SPh.

In various embodiments, optionally in combination with any other embodiment described herein, the palladium(II) catalyst contains at least one palladium-chlorine bond. In other embodiments, the palladium(II) catalyst is $Pd(CH_3CN)_2Cl_2$ or $Pd(OAc)_2$.

The present disclosure also provides in further embodiments the method described herein wherein the N-protected aminoacid ligand is selected from the group consisting of L1-L6:

L1

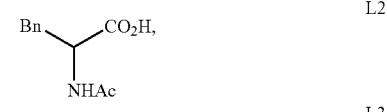
L2

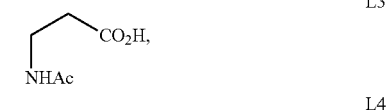
L3

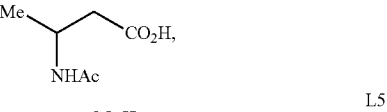
L4

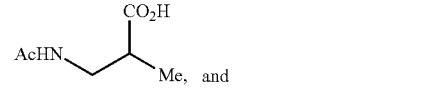
L5 and

-continued
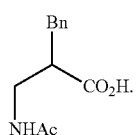 L6
In an embodiment, the N-protected aminoacid ligand is L5:
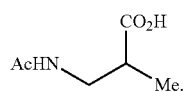 L5
In various embodiments, optionally in combination with any other embodiment described herein, the beta-lactone of formula (2) is one selected from the following table:
| 2a | 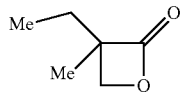 |
| --- | --- |
| 2b | 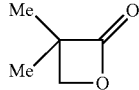 |
| 2c | 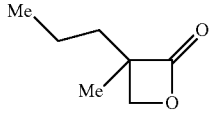 |
| 2d | 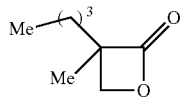 |
| 2e | 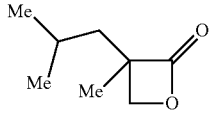 |
| 2f | 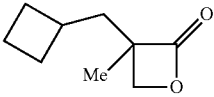 [SMILES: CC1(CC2CCC2)COC1=O] |
| 2g | 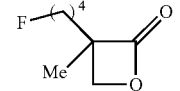 |
| 2h | 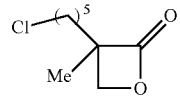 |
| 2i | 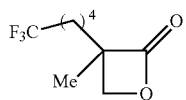 |
| 2j | 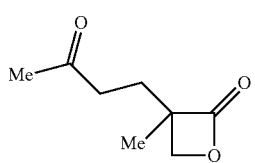 [SMILES: CC(=O)CCC1(C)COC1=O] |
| 2k | 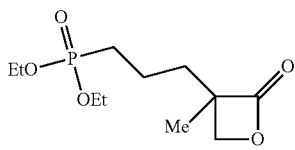 [SMILES: CCOP(=O)(CCCC1(C)COC1=O)OCC] |
| 2l | 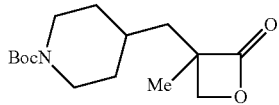 |
| 2m | 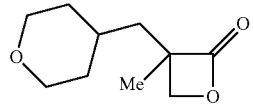 |
| 2n | 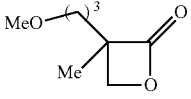 |
| 2o | 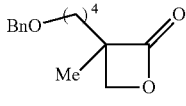 |
| 2p | 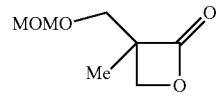 |
| 2q | 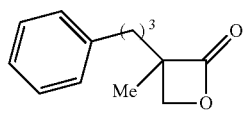 |
| 2r | 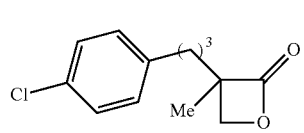 |
| 2s | 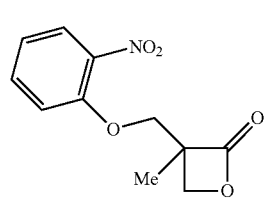 [SMILES: CC1(COc2ccccc2[N+](=O)[O-])COC1=O] |

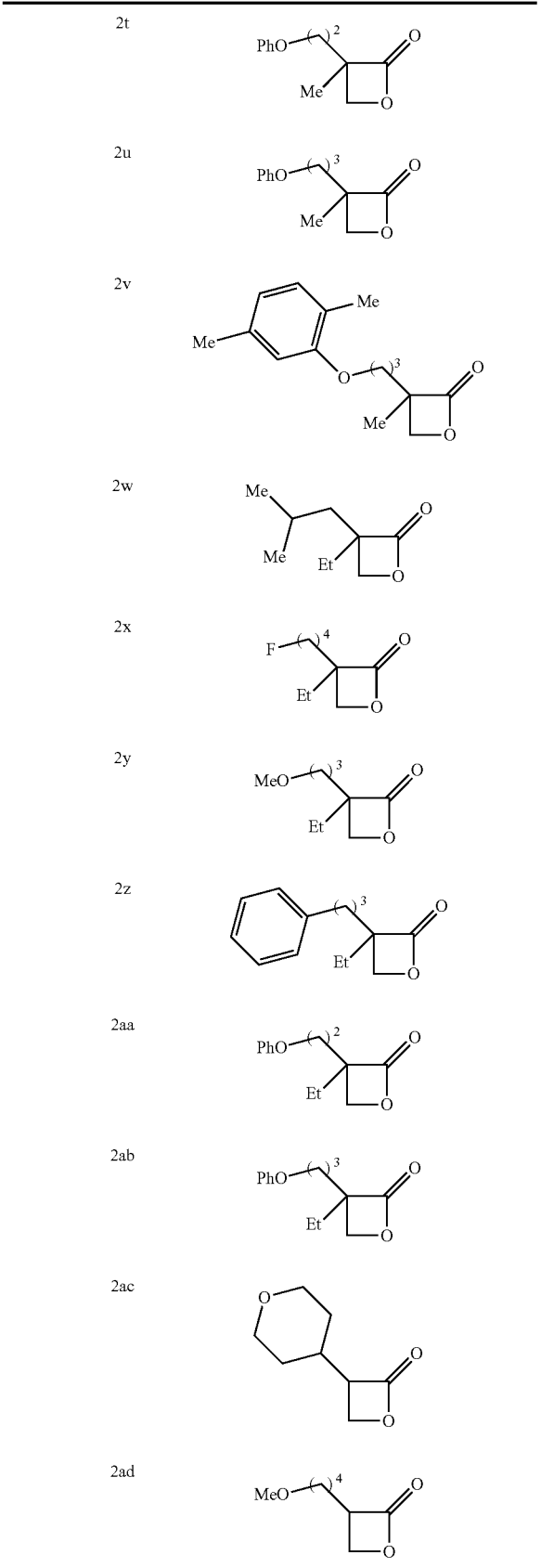

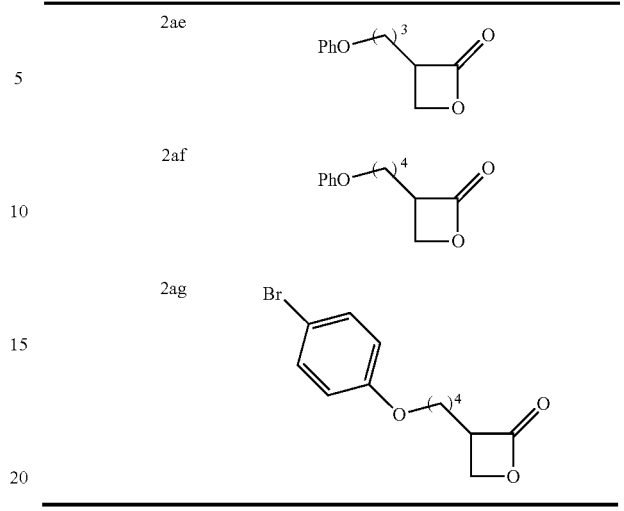

DETAILED DESCRIPTION

Definitions

Figure 1A:
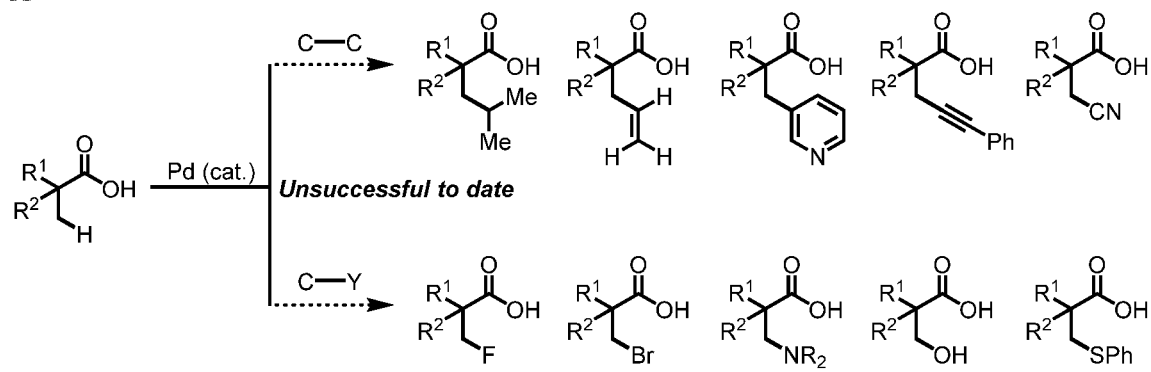
FIG. 1A-1C. Challenges in β-C(sp³)-H functionalizations (1A); A stepping stone strategy (1B); Ligand-enabled β-C—H lactonization (1C).
Figure 1B:
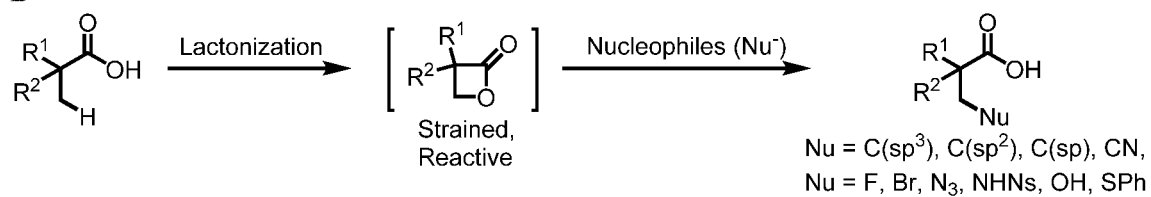
Figure 1C:
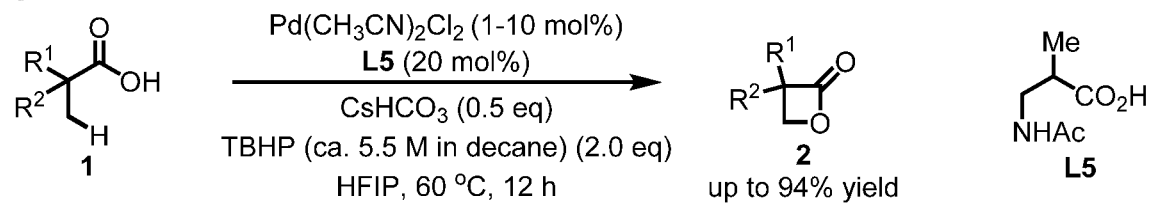

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, and the like. Thus, alkyl groups include primary alkyl groups, secondary alkyl groups, and tertiary alkyl groups. An alkyl group can be unsubstituted or optionally substituted with one or more substituents as described herein.

The term "alkoxy" refers to an —O-alkyl group having the indicated number of carbon atoms. For example, a (C₁-C₆)-alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "cycloalkyl" refers to a saturated monocyclic, bicyclic, tricyclic, or polycyclic, 3- to 14-membered ring system, such as a $C_3$-$C_8$-cycloalkyl. The cycloalkyl may be attached via any atom. Representative examples of cycloalkyl include, but are not limited to cyclopropyl, cyclobutyl, cyclopentyl, and cyclohexyl.

"Aryl" when used alone or as part of another term means a carbocyclic aromatic group whether or not fused having the number of carbon atoms designated or if no number is designated, up to 14 carbon atoms, such as a $C_6$-$C_{10}$-aryl or $C_6$-$C_{14}$-aryl. Examples of aryl groups include phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). An exemplary aryl is phenyl. An aryl group can be unsubstituted or optionally substituted with one or more substituents as described herein.

The term "heteroatom" refers to N, O, and S. Compounds of the present disclosure that contain N or S atoms can be optionally oxidized to the corresponding N-oxide, sulfoxide, or sulfone compounds.

"Heteroaryl," alone or in combination with any other moiety described herein, is a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

"Heterocycloalkyl" is a saturated or partially unsaturated non-aromatic monocyclic, bicyclic, tricyclic or polycyclic ring system that has from 3 to 14, such as 3 to 6, atoms in which 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

The present disclosure addresses the need, heretofore unsatisfied, for methods of carbon-heteroatom bond-forming reactions (fluorination, hydroxylation, amination etc.) based on β-C—H activation of free aliphatic acids (FIG. 1A). Disclosed herein is a method for the β-lactonization of ubiquitous aliphatic acids enabled by a Pd(II) catalyst bearing a mono-protected β-amino acid ligand. Highly practical advantages of the method include the use of inexpensive TBHP as a sole oxidant and purification by a simple aqueous work-up without chromatography. In addition, the diverse reactivity of the resultant β-lactones opens a new avenue for diverse formal β-C—H functionalization in exclusive monoselectivity and unparalleled scope.

In this context, β-Lactones are strained heterocycles that have received significant attention as valuable synthetic intermediates in natural and unnatural products synthesis (15). Due to their inherent ring strain, β-Lactones readily react with a wide range of nucleophiles by either acyl C—O or alkyl C—O bond cleavage, leading to myriad transformations. Accordingly, the β-lactonization of free carboxylic acids, in accordance with various embodiments of the present disclosure, is a useful methodology for accessing these diverse transformations. Moreover, the formation of the β-lactones from aliphatic acids ensures exclusive mono-selectivity and so provides an effective solution to a long-standing problem in β-C—H functionalizations.

In a pioneering example reported by Sen, a mixture of K$_2$PtCl$_4$, (17 mol %), K$_2$PtCl$_6$ (33 mol %) can promote the formation of γ-lactones from aliphatic acids in 16% yield, accompanied by 5% β-lactone (16, 17). γ-Lactonization of benzylic C—H bonds has also been reported using Pd and Pt catalysts (18, 19). In light of previous work using a by-standing oxidant to promote C—H activation/cyclization reactions (20, 21), we discovered catalysts and conditions for achieving an unprecedented β-C—H lactonization reaction. Compared to β-lactam formation, where a nucleophilic directing group can be employed to form a strong C—N bond (22), β-C—H lactonization is extremely challenging due to the low nucleophilicity of the carboxylic acid and the strain generated by a four-membered ring.

In one embodiment of the present disclosure, 2,2-dimethylbutyric acid (1a) was selected as an illustrative substrate for use in combination with a wide range of oxidants and catalysts. Through extensive experimentation, we found that the desired β-lactone 2a was formed in 15% NMR yield using a combination of Pd(CH$_3$CN)$_2$Cl$_2$, CsHCO$_3$ and hexafluoroisopropanol (HFIP) solvent. Per the methodology exemplified by this embodiment, no γ-lactone or β-, γ-hydroxylated products were observed during the reaction. Testing the reaction with other Pd(II) catalysts highlighted the Pd—Cl bond as favoring the selective C—O reductive elimination to form a lactone. In various embodiments, a readily available, inexpensive, and effective oxidant is t-butylhydroperoxide (TBHP) (4).

In accordance with various embodiments, the lactonization of formula (1) is catalyzed by a Pd(II) catalyst. Many simple Pd(II) salts are suitable for serving as, or are the precursors to in situ formation of, the catalyst. Examples include chloride salts, such as Pd(CH$_3$CN)$_2$Cl$_2$. Another example is Pd(OAc)$_2$. The catalyst is present in an effective amount, which is the minimum catalyst loading, expressed in mole percentage of substrate formula (1), to achieve the transformation of a formula (1) compound into a formula (2) compound. Exemplary catalyst loadings are in the range of about 0.1 to about 15 mol %, about 0.5 to about 10 mol %, and about 0.8 to about 3 mol %. In various embodiments, the catalyst is present in about 1, 2, 3, 4, 5, 6, 7, 8, 9, or about 10 mol %.

Figure 4:
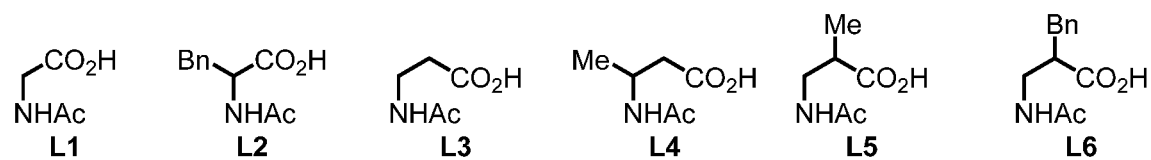
FIG. 4: Structures of Ligands of the N-monoprotected β-alanine class.

In various embodiments, the methods described herein are suitable for use with aminoacid ligands, such as N-protected aminoacid ligands (see. e.g., FIG. 4). In light of the recent advances in ligand accelerated Pd(II)-catalyzed C—H activation (23), we identified ligands that, in embodiments, significantly improve this reaction. Using the mono-N-protected α-amino acid (MPAA) ligand N-acetyl glycine L1, as an illustrative embodiment, the yield was improved to 36%. However, extensive modification of the backbone of the α-amino acid ligand gave minor improvements (40% yield with L2). Switching the ligand binding mode from five- to six-membered chelation, such as with commercially available N-acetyl β-alanine L3 under the same conditions, improved the yield to 48%. Building on this promising finding, we then investigated the influence of substituents on the ligand's side chain. Some substituents at the β-position slightly reduced the reactivity (L4), while substitution at the α-position proved beneficial (L5 to L6), with methyl-substituted L5 giving 65% yield. The isolated yield of desired β-lactone could be further improved to 73% when using TBHP in decane.

The amount of N-protected aminoacid ligand can vary and in general is adjusted to afford suitable conversion, yield, and observed rate of reaction. In various embodiments, the amount of ligand, expressed as mole percentage of substrate formula (1), is within the range of about 0.5 to about 30 mol %, about 1 to about 25 mol %, or about 2 to about 20 mol %. Exemplary amounts of ligand include about 1, about 2, about 5, about 10, about 15, about 20, about 25, and about 30 mol %.

Figure 2:
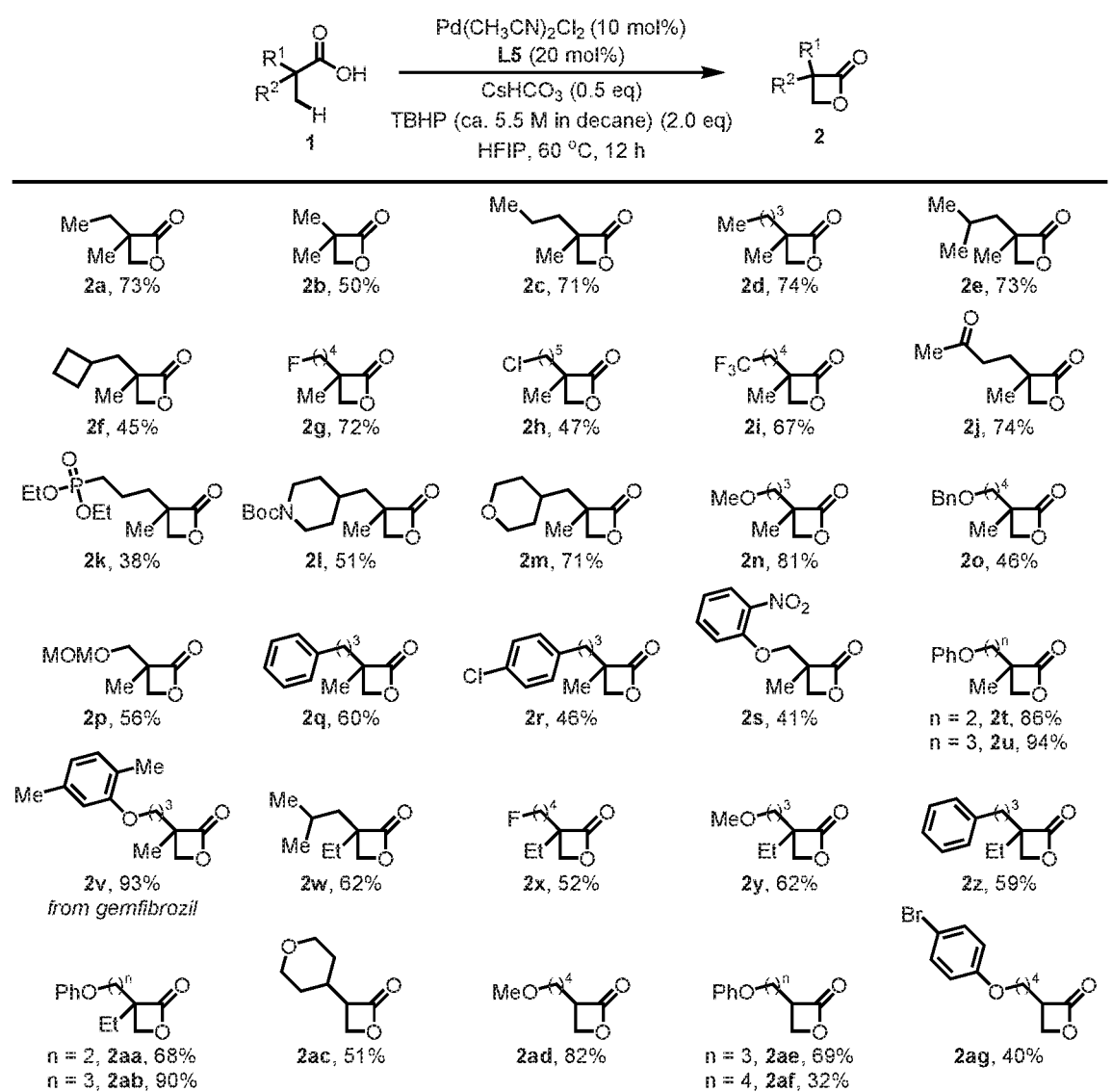
FIG. 2. Aliphatic acid scope for β-C(sp³)-H lactonization.

In various embodiments, the methods described herein are suitable for use with aliphatic carboxylic acids of formula (1) as defined herein. Exemplary carboxylic acids of formula (1) are represented in FIG. 2 as the beta-lactone product of formula (2). For example, aliphatic acids containing α-gem-dimethyl groups with various aliphatic chains including cyclobutanes (2f) were all compatible, affording the β-lactones (2a to 2f) in high yields. A range of functionalities such as fluoro (2g), chloro (2h), trifluoromethyl (2i), ketone (2j), and phosphoric ester (2k) were tolerated, with halogen (2h), ketone (2j) and phosphoric ester (2k) moieties serving as useful synthetic handles for subsequent derivatization. The lactone products containing a piperidine (2l) or a tetrahydropyran (2m) motif are useful embodiments. Different protecting groups on the hydroxyl group including simple methyl (Me) (2n), benzyl (Bn) (2o), and methoxymethyl (MOM) (2p) are well tolerated.

Aryl groups, such as phenyl (2q to 2r) and phenyl ether (2s to 2v) groups, also are useful in the methods described herein, and they remained intact despite the potentially reactive aryl or benzylic C—H bonds. In various embodiments, the aryl groups are optionally substituted with from one to three electron-donating (Me and O-alkyl) to electron-deficient (chloro, bromo, and nitro) groups, which are all well tolerated. Gemfibrozil (1v), an oral drug used to lower lipid levels (24), was converted to the corresponding β-lactone 2v in high yield. This lactone is useful as a versatile intermediate for library construction in medicinal chemistry. The remaining α-methyl group in these and other embodiments can undergo further C—H functionalizations to afford greater structural diversity. Tertiary aliphatic acids containing a single α-methyl group (2w to 2ab) consistently afforded useful yields, in addition to those substrates containing α-hydrogens (2ac to 2ag).

Figure 3:
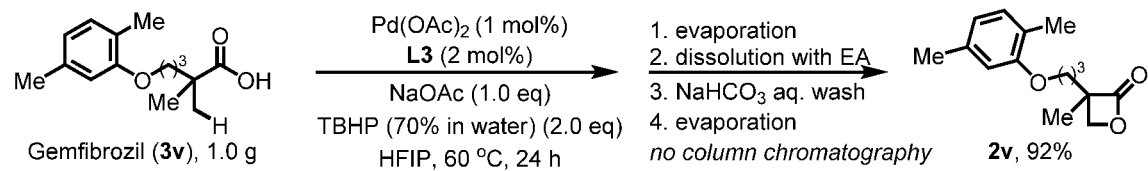
FIGS. 3A and 3B. Gram-scale β-lactonization of Gemfibrozil (3A), and mono-selective installation of nucleophiles (Nu) onto representative β-lactone 2v (3B).
Figure 3:
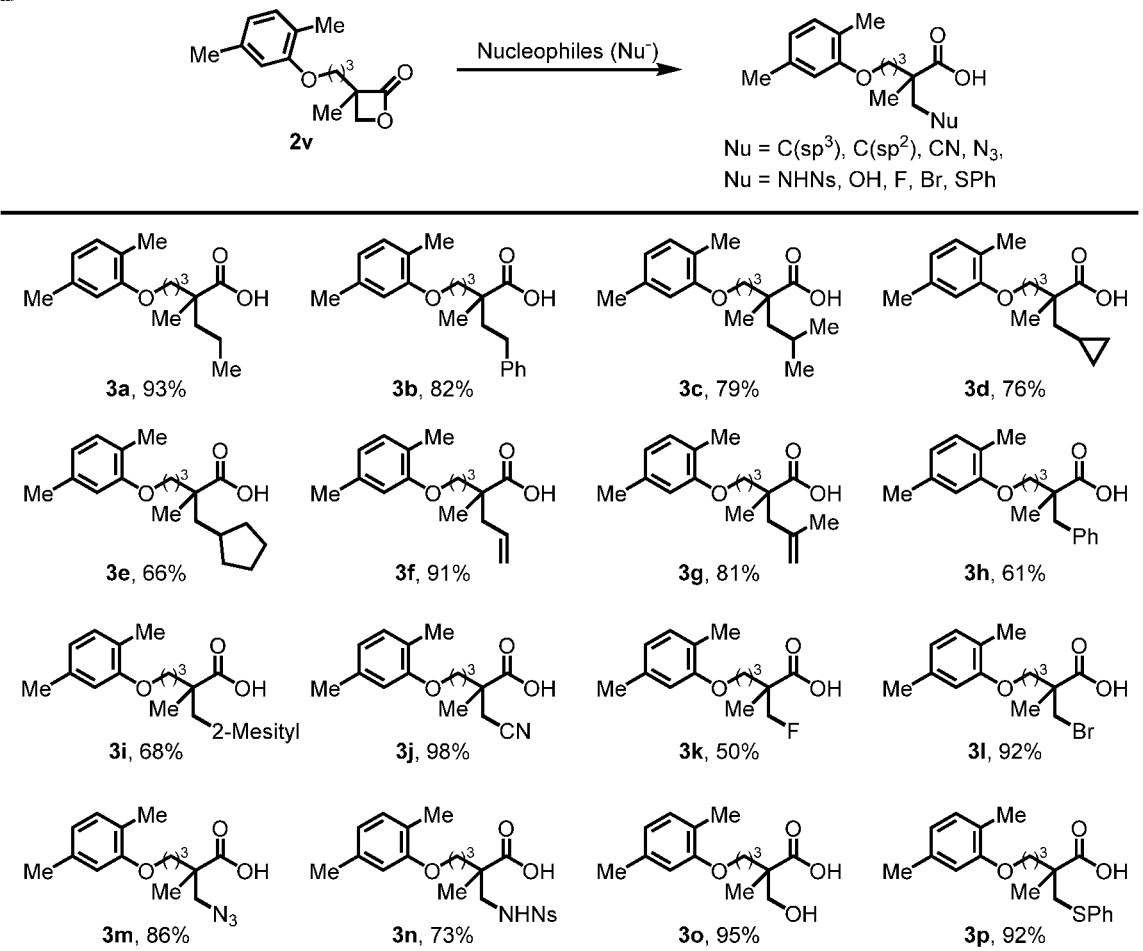

In an embodiment that demonstrates the scalability and practicality of the methodology described herein, we conducted a gram-scale s-lactonization of Gemfibrozil (1v) (FIG. 3A). Pure product (2v) was obtained by a simple aqueous wash without chromatography. Thus, in this embodiment, 1.0 g Gemfibrozil (1v) in HFIP, Pd(OAc)$_2$ (1.0 mmol %), commercially available MPAA ligand L3 (2.0 mmol %), and NaOAc (1.0 eq) were added to a reaction tube, followed by TBHP (70% in water) (2.0 eq). After stirring at 60° C. for 24 hrs, the HFIP solvent was removed by evaporation, followed by dissolution with ethyl acetate, which was washed with saturated NaHCO$_3$ solution to remove unreacted acid, ligand, and metal complex. Evaporation of the ethyl acetate delivered lactone product (2v) in 92% yield. From a practical standpoint, this reaction has several key advantages over other C—H activation protocols: (1) the inexpensive oxidant TBHP is used. (2) the reaction tolerates air and moisture; (3) the reaction may be reliably scaled-up; (4) a simple aqueous wash delivers the final product without chromatography.

As depicted in FIG. 3B, β-lactone product 2v is a stepping stone for mono-selective installation of a range of alkyl, alkenyl, aryl, halogen, amino, hydroxyl, and thiophenyl groups (25-27). Various alkyl (3a to 3e), alkenyl (3f to 3g), and aryl (3h to 3i) Grignard reagents in the presence of catalytic copper were able to successfully open the β-lactone to build new C—C bonds at the β-position of the parent aliphatic acids (25, 26). In various embodiments, secondary alkyl structure motifs such as isopropyl (3c), cyclopropyl (3d), and cyclopentyl (3e) are efficiently installed; in contrast, the analogous secondary alkyl iodides are usually incompatible in Pd-catalyzed C—H alkylation reactions.

In additional embodiments, β-Vinyl aliphatic acids (3f to 3g) are directly accessible through reaction with their corresponding vinyl (3f) and isopropenyl (3g) Grignard reagents. These embodiments, for example, provide a strategy that is complementary to the Pd catalyzed β-C—H olefination of free acids and their derivatives, where only electron-deficient olefins were effective.

In another embodiment, β-Lactone 2v is converted into corresponding β-arylated aliphatic acids (3h to 3i). This approach is useful in the case of 3i, for instance, because mesityl iodide is often not a viable coupling partner, owing to its steric bulk.

In still another embodiment, the nucleophile cyanide opens the lactone to construct a new C—C bond, affording the corresponding β-cyano aliphatic acids (3j). The electrophilicity of the f-lactone carbonyl was further illustrated in additional embodiments by the addition of the weak fluoride nucleophile (3k) to introduce a $CH_2F$ fragment, a highly sought-after bioisostere in medicinal chemistry. By a similar β-lactone opening, $MgBr_2$ delivered the formally β-brominated aliphatic acid (3l) in high yield; product 3l is a versatile compound for further elaboration.

In additional embodiments, manipulations of the β-lactone in the presence of hard nucleophiles $NaN_3$ and sodium 2-nitrophenylsulfonamide (NaNHNs) afforded valuable β-amino acid scaffolds 3m and 3n, respectively, in consistently high yields. By making use of the β-lactone as a masked aldol adduct, mild hydrolysis afforded the β-hydroxyl acid 3o in high yield. In addition, thiophenol sodium salt as a nucleophile is useful to obtain the formal β-chalcogenation product 3p in near quantitative yield.

Enumerated references cited in the disclosure hereinabove are as follows:

1 O. Daugulis, J. Roane, L. D. Tran, Bidentate, Monoanionic auxiliary-directed functionalization of carbon-hydrogen bonds. *Acc. Chem. Res.* 48, 1053-1064 (2015).
2 T. W. Lyons, M. S. Sanford, Palladium-catalyzed ligand-directed C—H functionalization reactions. *Chem. Rev.* 110, 1147-1169 (2010).
3 J. He, M. Wasa, K. S. L. Chan, Q. Shao, J.-Q. Yu, Palladium-catalyzed transformations of alkyl C—H Bonds. *Chem. Rev.* 117, 8754-8786 (2017).
4 R. Giri, J. Liang, J.-G. Lei, J.-J. Li, D.-H. Wang, X. Chen, I. C. Naggar, C. Guo, B. M. Foxman, J.-Q. Yu, Pd-catalyzed stereoselective oxidation of methyl groups by inexpensive oxidants under mild conditions: a dual role for carboxylic anhydrides in catalytic C—H bond oxidation. *Angew. Chem. Int. Ed* 44, 7420-7424 (2005).
5 R. Giri, N. Maugel, J.-J. Li, D.-H. Wang, S. P. Breazzano, L. B. Saunders. J.-Q Yu, Palladium-catalyzed methylation and arylation of $sp^2$ and $sp^3$ C—H bonds in simple carboxylic acids. *J. Am. Chem. Soc.* 129, 3510-3511 (2007).
6 D.-H. Wang, M. Wasa, R. Giri, J.-Q. Yu, Pd(II)-catalyzed cross-coupling of $sp^3$ C—H bonds with $sp^2$ and sp boronic acids using air as the oxidant. *J. Am. Chem. Soc.* 130, 7190-7191 (2008).
7 D. Shabashov, O. Daugulis, Auxiliary-assisted palladium-catalyzed arylation and alkylation of $sp^2$ and $sp^3$ carbon-hydrogen bonds *J. Am. Chem. Soc.* 132, 3965-3972 (2010).
8 S.-Y. Zhang, Q. Li, G. He, W. A. Nack, G. Chen, Stereoselective synthesis of β-alkylated α-amino acids via palladium-catalyzed alkylation of unactivated methylene $C(sp^3)$-H bonds with primary alkyl halides. *J. Am. Chem. Soc.* 135, 12135-12141 (2013).
9 Z. Zhuang, C.-B. Yu, G. Chen, Q.-F. Wu, Y. Hsiao, C. L. Joe, J. X. Qiao, M. A. Poss, J.-Q. Yu, Ligand-enabled β-$C(sp^3)$-H olefination of free carboxylic acids. *J. Am. Chem. Soc.* 140, 10363-10367 (2018).
10 M. Wasa, K. M. Engle, J.-Q. Yu, Pd(II)-catalyzed olefination of $sp^3$ C—H bonds. *J. Am. Chem. Soc.* 132, 3680-3681 (2010).
11 V. G. Zaitsev, D. Shabashov, O. Daugulis, Highly regioselective arylation of $sp^3$ C—H bonds catalyzed by palladium acetate. *J. Am. Chem. Soc.* 127, 13154-13155 (2005).
12 G. Chen, Z. Zhuang, G.-C. Li, T. G. Saint-Denis, Y. Hsiao, C. L. Joe, J.-Q. Yu, Ligand-enabled β-C—H arylation of α-amino acids without installing exogenous directing groups. *Angew. Chem. Int. Ed.* 56, 1506-1509 (2017).
13 Y. Zhu, X. Chen, C. Yuan, G. Li, J. Zhang, Y. Zhao, Pd-catalysed ligand-enabled carboxylate-directed highly regioselective arylation of aliphatic acids. *Nat. Commun.* 8, 14904-14911 (2017).
14 P.-X. Shen, L. Hu, Q. Shao, K. Hong, J.-Q. Yu, Pd(II)-catalyzed enantioselective $C(sp^3)$-H arylation of free carboxylic acids. *J. Am. Chem. Soc.* 140, 6545-6549 (2018).
15 Y. Wang, R. L. Tennyson, D. Romo, β-Lactones as intermediates for natural product total synthesis and new transformations. *Heterocycles* 64, 605-658 (2004).
16 L.-C. Kao, A. Sen, Platinum(II) catalysed selective remote oxidation of unactivated C—H bonds in aliphatic carboxylic acids. *J. Chem. Soc., Chem. Commun.* 1242-1243 (1991).
17 B. D. Dangel, J. A. Johnson, D. Sames, Selective functionalization of amino acids in water: a synthetic method via catalytic C—H bond activation. *J. Am. Chem. Soc.* 123, 8149-8150 (2001).
18 J. M. Lee, S. Chang, Pt-Catalyzed $sp^3$ C—H bond activation of o-alkyl substituted aromatic carboxylic acid derivatives for the formation of aryl lactones. *Tetrahedron Lett.* 47, 1375-1379 (2006).
19 P. Novák, A. Correa. J. Gallardo-Donaire, R. Martin, Synergistic palladium-catalyzed $C(sp^3)$-H activation/C$(sp^3)$-O bond formation: a direct, step-economical route to benzolactones. *Angew. Chem. Int. Ed.* 50, 12236-12239 (2011).
20 T.-S. Mei, X. Wang, J.-Q. Yu, Pd(II)-catalyzed amination of C—H Bonds using single-electron or two-electron oxidants. *J. Am. Chem. Soc.* 131, 10806-10807 (2009).
21 K. M. Engle, T.-S. Mei, X. Wang, J.-Q. Yu, Bystanding $F^+$ oxidants enable selective reductive elimination from high-valent metal centers in catalysis. *Angew. Chem. Int. Ed.* 50, 1478-1491 (2011).
22 Q. Zhang, K. Chen, W. Rao, Y. Zhang, F.-J. Chen, B.-F. Shi, Stereoselective synthesis of chiral α-amino-β-lactams through palladium(II)-catalyzed sequential monoarylation/amidation of C(sp³)-H Bonds. *Angew. Chem. Int. Ed* 52, 13588-13592 (2013).

23 D.-H. Wang, K. M. Engle, B.-F. Shi, J.-Q. Yu, Ligand-enabled reactivity and selectivity in a synthetically versatile aryl C—H olefination. *Science* 327, 315-319 (2010).

24 P. A. Todd, A. Ward, Gemfibrozil—a review of its pharmacodynamic and pharmacokinetic properties, and therapeutic use in dyslipidaemia. *Drugs* 36, 314-339 (1988).

25 M. Kawashima. T. Sato, T. Fujisawa, A facile method for synthesis of three carbon-homologated carboxylic acid by regioselective ring-opening of β-propiolactones with organocopper reagents. *Tetrahedron* 45, 403-412 (1989).

26 N. D. Smith, A. M. Wohlrab, M. Goodman, Enantiocontrolled synthesis of α-methyl amino acids via Bn₂N-α-methylserine-β-lactone. *Org. Lett.* 7, 255-258 (2005).

27 L. D. Arnold, T. H. Kalantar, J. C. Vederas, Conversion of serine to stereochemically pure β-substituted α-amino acids via β-Lactones. *J. Am. Chem. Soc.* 107, 7105-7109 (1985).

Examples

Additional embodiments of the disclosure include the following examples.

General Information: HFIP was obtained from Oakwood and other solvents were obtained from Sigma-Aldrich, Alfa-Aesar, and Acros and used directly without further purification. Pd(CH₃CN)₂Cl₂ and Pd(OAc)₂ were obtained from Strem. Ag₂CO₃ was purchased from Sigma-Aldrich. Carboxylic acids were obtained from the commercial sources or synthesized following literature procedures. Other reagents were purchased at the highest commercial quality and used without further purification, unless otherwise stated. Analytical thin layer chromatography was performed on 0.25 mm silica gel 60-F254. Visualization was carried out with short-wave UV light or KMnO₄ and heat as developing agents. ¹H NMR spectra were recorded on Bruker DRX-600, DRX-500, and AMX-400 instruments. Chemical shifts were quoted in parts per million (ppm) referenced to 0.0 ppm for TMS. The following abbreviations (or combinations thereof) were used to explain multiplicities: s=singlet, d=doublet, t=triplet, q=quartet, m=multiplet, br=broad. Coupling constants, J, were reported in Hertz unit (Hz). ¹³C NMR spectra were recorded on Bruker DRX-600 and DRX-500 and were fully decoupled by broad band proton decoupling. Chemical shifts were reported in ppm referenced to the center line of a triplet at 77.0 ppm of CDC3. Column chromatography was performed using E. Merck silica (60, particle size 0.043-0.063 mm), and pTLC was performed on Merck silica plates (60F-254). High-resolution mass spectra (HRMS) were recorded on an Agilent Mass spectrometer using ESI-TOF (electrospray ionization-time of flight).

General Procedure for β-C(sp³)-H Lactonization

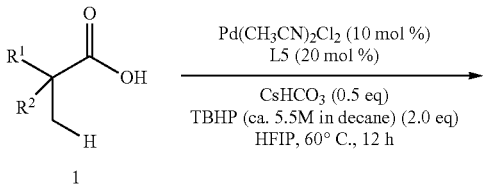

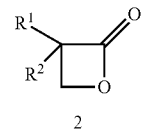

General Procedure A: In the culture tube, Pd(CH₃CN)₂Cl₂ (10 mol %. 2.6 mg), ligand L5 (20 mol %, 2.9 mg), CsHCO₃ (0.5 eq, 9.7 mg), and carboxylic acid 1 (0.1 mmol) in order were weighed in air and placed with a magnetic stir bar. Then HFIP (1.0 mL) and TBHP (ca. 5.5 M in decane) (2.0 eq, 36 uL) were added. The reaction mixture was stirred at rt for 3 min. and then heated to 60° C. for 12 h (600 rpm). After being allowed to cool to room temperature, the mixture was concentrated in vacuo, and the resulting mixture purified by pTLC as the eluent or dissolution with EA and saturated NaHCO₃ aqueous wash.

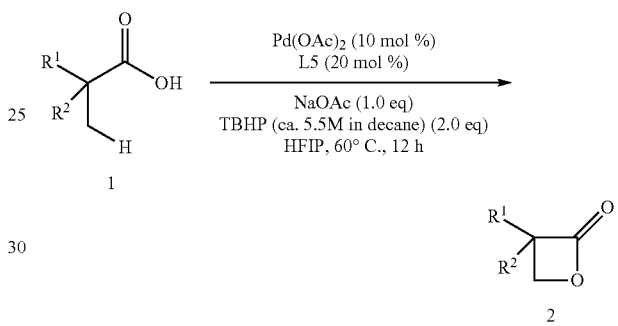

General Procedure B: In the culture tube, Pd(OAc)₂ (10 mol %, 2.2 mg), ligand L5 (20 mol %, 2.9 mg), NaOAc (1.0 eq. 8.2 mg), and carboxylic acid 1 (0.1 mmol) in order were weighed in air and placed with a magnetic stir bar. Then HFIP (1.0 mL) and TBHP (ca. 5.5 M in decane) (2.0 eq, 36 µL) were added. The reaction mixture was stirred at it for 3 min, and then heated to 60° C. for 12 h (600 rpm). After being allowed to cool to room temperature, the mixture was concentrated in vacuo, and the resulting mixture purified by pTLC as the eluent or dissolution with EA and saturated NaHCO₃ aqueous wash.

Substrate Scope for β-C(sp³)-H Lactonization

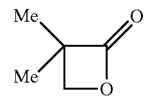

Following General Procedure A on 0.1 mmol scale. Due to the volatility of the product, the yield was determined by ¹H NMR analysis of the crude product using CH₂Br₂ (0.1 mmol, 7 uL) as the internal standard (50% yield).

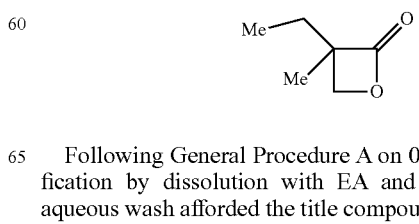

Following General Procedure A on 0.1 mmol scale. Purification by dissolution with EA and saturated NaHCO₃ aqueous wash afforded the title compound (colorless oil, 8.3 mg, 73% yield). ¹H NMR (600 MHz, CDCl₃) δ 4.16 (d, J=5.0 Hz, 1H), 4.03 (d, J=5.0 Hz, 1H), 1.81-1.68 (m, 2H), 1.42 (s, 3H), 1.03 (t, J=7.5 Hz, 3H); ¹³C NMR (150 MHz, CDCl₃) δ 175.04, 71.02, 58.00, 27.38, 18.97, 8.98.

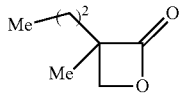

Following General Procedure on 0.1 mmol scale. Purification by dissolution with EA and saturated NaHCO₃ aqueous wash afforded the title compound (colorless oil, 9.1 mg, 71% yield). ¹H NMR (600 MHz, CDCl₃) δ 4.16 (d, J=5.0 Hz, 1H), 4.02 (d, J=5.0 Hz, 1H), 1.71-1.65 (m, 2H), 1.59-1.48 (m, 2H), 1.42 (s, 3H), 0.97 (t, J=7.3 Hz, 4H); ¹³C NMR (150 MHz, CDCl₃) δ 175.15, 71.55, 57.48, 36.57, 19.33, 18.05, 14.31.

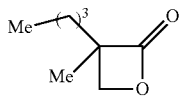

Following General Procedure on 0.1 mmol scale. Purification by dissolution with EA and saturated NaHCO₃ aqueous wash afforded the title compound (colorless oil, 10.5 mg, 74% yield). ¹H NMR (600 MHz, CDCl₃) δ 4.16 (d, J=5.0 Hz, 1H), 4.02 (d, J=5.0 Hz, 1H), 1.76-1.64 (m, 2H), 1.51-1.44 (m, 114), 1.42 (s, 3H), 1.39-1.27 (m, 3H), 0.93 (t, J=7.2 Hz, 3H); ¹³C NMR (150 MHz, CDCl₃) δ 175.20, 71.53, 57.44, 34.16, 26.80, 22.94, 19.35, 13.99.

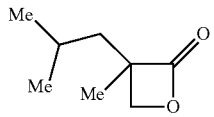

Following General Procedure on 0.1 mmol scale. Purification by dissolution with EA and saturated NaHCO₃ aqueous wash afforded the title compound (colorless oil, 10.4 mg, 73% yield). ¹H NMR (600 MHz, CDCl₃) δ 4.21 (d, J=5.0 Hz, 1H), 4.06 (dd, J=5.0, 0.8 Hz, 1H), 1.87-1.78 (m, 1H), 1.78-1.71 (m, 1H), 1.61-1.55 (m, 1H), 1.42 (s, 3H), 0.99 (d, J=6.6 Hz, 3H), 0.88 (d, J=6.6 Hz, 3H); ¹³C NMR (150 MHz, CDCl₃) δ 175.54, 72.80, 56.75, 42.64, 24.80, 23.97, 22.35, 18.92.

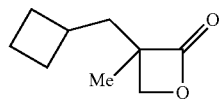

Following General Procedure on 0.1 mmol scale. Purification by dissolution with EA and saturated NaHCO₃ aqueous wash afforded the title compound (colorless oil, 7.0 mg, 45% yield). ¹H NMR (600 MHz, CDCl₃) δ 4.16 (d, J=5.0 Hz, 1H), 3.98 (d, J=5.0 Hz, 1H), 2.52-2.41 (m, 1H), 2.16-2.01 (m, 2H), 1.95-1.87 (m, 1H), 1.87-1.75 (m, 3H), 1.75-1.66 (m, 2H), 1.38 (s, 3H); ¹³C NMR (150 MHz, CDCl₃) δ 175.14, 71.48, 57.19, 41.37, 32.64, 30.00, 29.41, 19.72, 19.15.

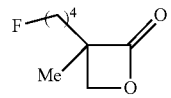

Following General Procedure on 0.1 mmol scale. Purification by dissolution with EA and saturated NaHCO₃ aqueous wash afforded the title compound (colorless oil, 11.5 mg, 72% yield). ¹H NMR (600 MHz, CDCl₃) δ 4.48 (dt, J=47.2, 5.9 Hz, 2H), 4.18 (d, J=5.1 Hz, 1H), 4.06 (d, J=5.1 Hz, 1H), 1.82-1.70 (m, 4H), 1.70-1.60 (m, 1H), 1.55-1.47 (m, 1H), 1.45 (s, 3H); ¹³C NMR (150 MHz, CDCl₃) δ 174.91, 83.67 (d, J=165.0 Hz), 71.45, 57.31, 34.04, 30.50 (d, J=19.9 Hz), 20.69 (d, J=4.9 Hz), 19.25; HRMS (ESI-TOF) Calcd for C₈H₁₄FO₃ [M+H]⁺: 161.0978; found: 161.0975.

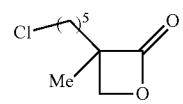

Following General Procedure on 0.1 mmol scale. Purification by dissolution with EA and saturated NaHCO₃ aqueous wash afforded the title compound (colorless oil, 9.0 mg, 47% yield). ¹H NMR (600 MHz, CDCl₃) δ 4.15 (d, J=5.0 Hz, 1H), 4.04 (d, J=5.0 Hz, 1H), 3.54 (t, J=6.6 Hz, 2H), 1.86-1.75 (m, 2H), 1.75-1.66 (m. 2H), 1.55-1.46 (m. 2H), 1.43 (s, 3H). 1.40-1.29 (m, 2H); ¹³C NMR (150 MHz, CDCl₃) δ 174.90, 71.48, 57.36, 44.93, 34.34, 32.39, 27.05, 24.04, 19.38; HRMS (ESI-TOF) Calcd for C₉H₁₆ClO₂ [M+H]⁺: 191.0839; found: 191.0827.

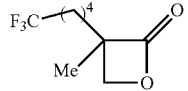

Following General Procedure on 0.1 mmol scale. Purification by dissolution with EA and saturated NaHCO₃ aqueous wash afforded the title compound (colorless oil, 14.0 mg, 67% yield). ¹H NMR (600 MHz, CDCl₃) δ 4.15 (d, J=5.1 Hz, 1H), 4.05 (d, J=5.1 Hz, 1H), 2.18-2.00 (m, 2H), 1.77-1.68 (m, 2H), 1.67-1.50 (m, 4H), 1.43 (s, 3H); ¹³C NMR (150 MHz, CDCl₃) δ 174.70, 127.10 (q, J=276.4 Hz), 71.45, 57.20, 34.14, 33.60 (q, J=28.6 Hz), 23.84, 22.18 (q, J=2.9 Hz), 19.31; HRMS (ESI-TOF) Calcd for C₉H₁₄F₃O₂ [M+H]⁺: 211.0946; found: 211.0949.

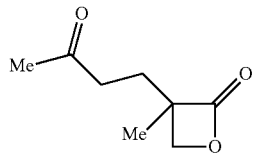

Following General Procedure on 0.1 mmol scale. Purification by dissolution with EA and saturated NaHCO₃ aqueous wash afforded the title compound (colorless oil, 11.6 mg, 74% yield). ¹H NMR (600 MHz, CDCl₃) δ 3.84 (d, J=8.7 Hz, 1H), 3.80 (dd, J=8.7, 2.9 Hz, 1H), 2.19-2.08 (m, 1H), 2.08-1.99 (m, 1H), 1.88-1.79 (m, 2H), 1.56 (s, 3H), 1.16 (s. 3H); ¹³C NMR (150 MHz, CDCl₃) δ 208.49, 175.48, 72.09, 38.26, 31.38, 28.95, 24.30, 16.40; HRMS (ESI-TOF) Calcd for $C_8H_{13}O_3$ $[M+H]^+$: 157.0865; found: 157.0863.

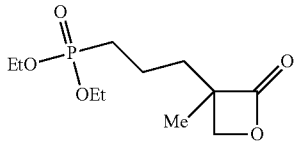 [SMILES: CCOP(=O)(CCCC1(C)COC1=O)OCC]

Following General Procedure on 0.1 mmol scale. Purification by dissolution with EA and saturated $NaHCO_3$ aqueous wash afforded the title compound (colorless oil, 10.0 mg, 38% yield). $^1H$ NMR (600 MHz, $CDCl_3$) δ 4.17 (d, J=5.2 Hz, 1H), 4.15-4.05 (m, 4H), 4.04 (d, J=5.2 Hz, 1H), 1.87-1.68 (m, 6H), 1.44 (s, 3H), 1.33 (t, J=7.1 Hz, 6H); $^{13}C$ NMR (150 MHz, $CDCl_3$) δ 174.53, 71.37, 61.94 (d, J=6.7 Hz), 61.93 (d, J=6.8 Hz), 57.17 (d, J=1.7 Hz), 35.09 (d, J=16.0 Hz), 25.70 (d, J=142.3 Hz), 19.16, 18.03 (d, J=4.9 Hz), 16.57 (d, J=5.9 Hz); HRMS (ESI-TOF) Calcd for $C_{11}H_{22}O_5P$ $[M+H]^+$: 265.1205; found: 265.1208.

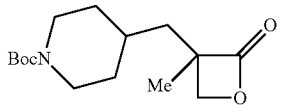 [SMILES: CC(C)(C)OC(=O)N1CCC(CC2(C)COC2=O)CC1]

Following General Procedure on 0.1 mmol scale. Purification by dissolution with EA and saturated $NaHCO_3$ aqueous wash afforded the title compound (colorless oil, 14.5 mg, 51% yield). $^1H$ NMR (600 MHz, $CDCl_3$) δ 4.16 (d, J=5.1 Hz, 1H), 4.11 (br s, 2H), 4.06 (d, J=5.0 Hz, 1H), 2.68 (br s, 2H), 1.79-1.57 (m, 7H), 1.45 (s, 9H), 1.21 (s, 3H); $^{13}C$ NMR (150 MHz, $CDCl_3$) δ 175.00, 154.90, 79.69, 56.31, 40.73, 33.24, 33.06, 32.66, 28.59, 28.57.

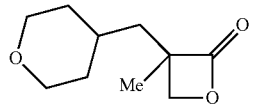 [SMILES: CC1(CC2CCOCC2)COC1=O]

Following General Procedure on 0.1 mmol scale. Purification by dissolution with EA and saturated $NaHCO_3$ aqueous wash afforded the title compound (colorless oil, 13.0 mg, 71% yield). $^1H$ NMR (600 MHz, $CDCl_3$) δ 4.18 (d, J=5.1 Hz, 1H), 4.06 (d, J=5.1 Hz, 1H), 4.00-3.91 (m, 2H), 3.45-3.33 (m, 2H), 1.79-1.70 (m, 2H), 1.70-1.62 (m, 2H), 1.54-1.47 (m, 1H), 1.44 (s, 3H), 1.42-1.34 (m, 2H); $^{13}C$ NMR (150 MHz, $CDCl_3$) δ 175.03, 72.48, 67.96, 67.72, 56.28, 41.11, 33.86, 33.21, 31.68, 19.32; HRMS (ESI-TOF) Calcd for $C_{10}H_{17}O_3$ $[M+H]^+$: 185.1178; found: 185.1172.

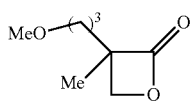

Following General Procedure on 0.1 mmol scale. Purification by dissolution with EA and saturated $NaHCO_3$ aqueous wash afforded the title compound (colorless oil, 12.8 mg, 81% yield). $^1H$ NMR (600 MHz, $CDCl_3$) δ 4.17 (d, J=5.0 Hz, 1H), 4.04 (d, J=5.0 Hz, 1H), 3.41 (t, J=5.8 Hz, 2H), 3.33 (s, 3H), 1.83-1.70 (m, 3H), 1.67-1.57 (m, 1H), 1.43 (s, 3H); $^{13}C$ NMR (150 MHz, $CDCl_3$) δ 175.08, 72.21, 71.62, 58.70, 57.08, 31.16, 24.82, 19.20; HRMS (ESI-TOF) Calcd for $C_8H_{15}O_3$ $[M+H]^+$: 159.1021; found: 159.1022.

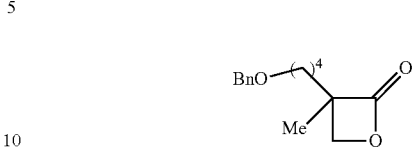

Following General Procedure on 0.1 mmol scale. Purification by pTLC afforded the title compound (colorless oil, 11.5 mg, 46% yield). $^1H$ NMR (600 MHz, $CDCl_3$) δ 7.41-7.31 (m, 3H), 7.31-7.26 (m, 2H), 4.50 (s, 2H), 4.15 (d, J=5.0 Hz, 1H), 4.01 (d, J=5.0 Hz, 1H), 3.48 (t, J=6.2 Hz, 2H), 1.78-1.56 (m, 6H), 1.41 (s, 3H); $^{13}C$ NMR (150 MHz, $CDCl_3$) δ 175.02, 138.56, 128.55, 127.84, 127.76, 73.17, 71.49, 69.87, 57.42, 34.23, 29.92, 21.52, 19.30.

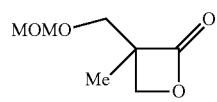

Following General Procedure on 0.1 mmol scale. Purification by dissolution with EA and saturated $NaHCO_3$ aqueous wash afforded the title compound (colorless oil, 9.0 mg, 56% yield). $^1H$ NMR (600 MHz, $CDCl_3$) δ 5.42-5.33 (m, 2H), 4.16 (d, J=11.3 Hz, 1H), 3.77-3.72 (m, 2H), 3.35 (s, 3H), 3.23 (d, J=9.2 Hz, 1H), 1.31 (s, 3H); $^{13}C$ NMR (150 MHz, $CDCl_3$) δ 171.68, 95.10, 75.53, 72.35, 59.53, 45.96, 20.89; HRMS (ESI-TOF) Calcd for $C_7H_{13}O_4$ $[M+H]^+$: 161.0814; found: 161.0821.

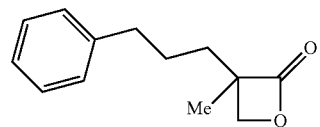 [SMILES: CC1(CCCc2ccccc2)COC1=O]

Following General Procedure on 0.1 mmol scale. Purification by pTLC afforded the title compound (colorless oil, 12.3 mg, 60% yield). $^1H$ NMR (400 MHz, $CDCl_3$) δ 7.35-7.23 (m, 2H), 7.23-7.14 (m, 3H), 4.12 (d, J=5.0 Hz, 1H), 4.01 (d, J=5.0 Hz, 1H), 2.66 (t, J=7.2 Hz, 2H), 1.88-1.77 (m, 1H), 1.77-1.61 (m, 3H), 1.41 (s, 3H); $^{13}C$ NMR (150 MHz, $CDCl_3$) δ 174.92, 141.46, 128.60, 128.50, 126.21, 71.45, 57.33, 35.89, 33.93, 26.41, 19.36.

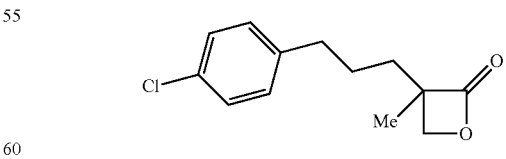

Following General Procedure on 0.1 mmol scale. Purification by pTLC afforded the title compound (colorless oil, 11.0 mg, 46% yield). $^1H$ NMR (600 MHz, $CDCl_3$) δ 7.25 (d, J=8.4 Hz, 2H), 7.10 (d, J=8.4 Hz, 2H), 4.11 (d, J=5.0 Hz, 1H), 4.01 (d. J=5.0 Hz, 1H), 2.67-2.58 (m, 2H), 1.84-1.75 (m. 1H), 1.75-1.66 (m, 2H), 1.68-1.59 (m, 1H), 1.41 (s, 3H);

$^{13}$C NMR (150 MHz, CDCl$_3$) δ 174.77, 139.86, 131.97, 129.84, 128.71, 71.42, 57.27, 35.21, 33.85, 26.30, 19.38.

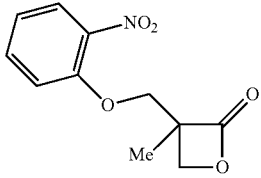 [SMILES: CC1(COc2ccccc2[N+](=O)[O-])COC1=O]

Following General Procedure on 0.1 mmol scale. Purification by pTLC afforded the title compound (colorless oil, 9.7 mg, 41% yield). $^1$H NMR (600 MHz, CDCl$_3$) δ 7.90 (dd, J=8.1, 1.7 Hz, 1H), 7.56 (ddd, J=8.6, 7.5, 1.7 Hz, 1H), 7.17-7.07 (m, 2H). 4.69 (d, J=5.1 Hz, 1H), 4.36 (d, J=9.5 Hz, 1H), 4.19 (d, J=5.1 Hz, 1H), 4.11 (d, J=9.5 Hz, 1H), 1.58 (s, 3H); $^{13}$C NMR (150 MHz, CDCl$_3$) δ 185.74, 172.18, 151.43, 134.50, 126.11, 122.01, 115.63, 69.93, 69.49, 57.76, 16.45; HRMS (ESI-TOF) Calcd for C$_{11}$H$_{12}$NO$_5$ [M+H]$^+$: 238.0715; found: 238.0716.

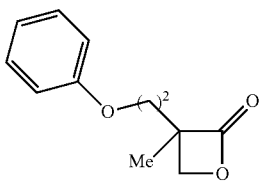

Following General Procedure on 0.1 mmol scale. Purification by pTLC afforded the title compound (colorless oil, 17.8 mg, 86% yield). $^1$H NMR (600 MHz, CDCl$_3$) δ 7.33-7.27 (m, 2H), 7.01-6.94 (m, 1H), 6.90-6.85 (m, 2H), 4.47 (d, J=5.1 Hz, 1H), 4.20-4.13 (m, 1H), 4.14-4.08 (m, 2H), 2.39-2.30 (m, 1H), 2.16-2.08 (m, 1H), 1.50 (s, 3H); $^{13}$C NMR (150 MHz, CDCl$_3$) δ 174.77, 158.38, 129.73, 121.40, 114.49, 72.45, 63.66, 55.63, 33.25, 19.03; HRMS (ESI-TOF) Calcd for C$_{12}$H$_{15}$O$_3$ [M+H]$^+$: 207.1021; found: 207.1029.

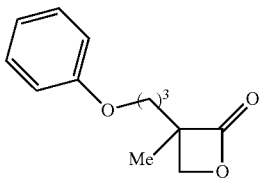

Following General Procedure on 0.1 mmol scale. Purification by pTLC afforded the title compound (colorless oil, 20.7 mg, 94% yield). $^1$H NMR (600 MHz, CDCl$_3$) δ 7.31-7.26 (m, 2H), 6.98-6.92 (m, 1H), 6.90-6.86 (m, 2H), 4.18 (d, J=5.1 Hz, 1H), 4.06 (d, J=5.1 Hz, 1H), 3.99 (t, J=5.8 Hz, 2H), 2.04-1.94 (m, 1H), 1.94-1.89 (m, 2H), 1.88-1.77 (m, 1H), 1.47 (s. 3H); $^{13}$C NMR (150 MHz, CDCl$_3$) δ 174.81, 158.80, 129.63, 120.99, 114.52, 71.65, 67.24, 57.08, 31.23, 24.65, 19.23; HRMS (ESI-TOF) Calcd for C$_{13}$H$_{17}$O$_3$ [M+H]$^+$: 221.1178; found: 221.1181.

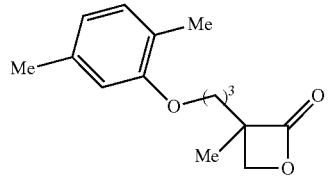

Following General Procedure on 0.1 mmol scale. Purification by pTLC afforded the title compound (colorless oil, 23.0 mg, 93% yield). $^1$H NMR (600 MHz, CDCl$_3$) δ 7.01 (d, J=7.5 Hz, 1H), 6.68 (d, J=7.5 Hz, 1H). 6.61 (s, 1H), 4.19 (d, J=5.1 Hz, 1H), 4.07 (d, J=5.1 Hz, 1H), 4.03-3.92 (m, 2H), 2.31 (s, 3H), 2.17 (s, 3H), 2.04-1.98 (m, 1H), 1.98-1.90 (m, 2H), 1.90-1.78 (m, 1H), 1.48 (s, 3H); $^{13}$C NMR (150 MHz, CDCl$_3$) δ 174.82, 156.78, 136.72, 130.55, 123.62, 121.13, 112.03, 71.66, 67.24, 57.14, 31.33, 24.86, 21.54, 19.26, 15.94; HRMS (ESI-TOF) Calcd for C$_{15}$H$_{21}$O$_3$ [M+H]$^+$: 249.1491; found: 249.1492.

Following General Procedure on 0.1 mmol scale. Purification by dissolution with EA and saturated NaHCO$_3$ aqueous wash afforded the title compound (colorless oil, 9.7 mg, 62% yield). $^1$H NMR (600 MHz, CDCl$_3$) δ 4.16 (d, J=5.2 Hz, 1H), 4.11 (d, J=5.2 Hz, 1H), 1.84-1.74 (m, 4H), 1.62-1.55 (m, 1H), 1.04 (t, J=7.5 Hz, 3H), 0.99 (d, J=6.4 Hz, 3H), 0.88 (d, J=6.5 Hz, 3H); $^{13}$C NMR (150 MHz, CDCl$_3$) δ 174.86, 70.11, 61.45, 40.97, 25.20, 24.68, 24.13, 22.54, 8.88; HRMS (ESI-TOF) Calcd for C$_9$H$_{17}$O$_2$ [M+H]$^+$: 157.1229; found: 157.1226.

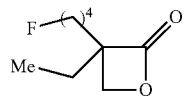

Following General Procedure on 0.1 mmol scale. Purification by dissolution with EA and saturated NaHCO$_3$ aqueous wash afforded the title compound (colorless oil, 9.0 mg, 52% yield). $^1$H NMR (600 MHz, CDCl$_3$) δ 4.47 (dt, J=46.9, 5.6 Hz, 2H), 4.12 (d, J=5.7 Hz, 1H), 4.11 (d, J=5.7 Hz, 1H), 1.85-1.67 (m, 5H), 1.67-1.59 (m, 1H), 1.53-1.39 (m, 2H), 1.03 (t, J=7.5 Hz, 3H); $^{13}$C NMR (151 MHz, CDCl$_3$) δ 174.28, 83.69 (d, J=165.1 Hz), 68.72, 62.13, 31.93, 30.61 (d, J=19.9 Hz), 25.43, 20.55 (d, J=4.8 Hz), 8.85; HRMS (ESI-TOF) Calcd for C$_9$H$_{16}$FO$_2$ [M+H]$^+$: 175.1134; found: 175.1135.

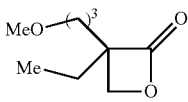

Following General Procedure on 0.1 mmol scale. Purification by dissolution with EA and saturated NaHCO$_3$ aqueous wash afforded the title compound (colorless oil, 10.7 mg, 62% yield). $^1$H NMR (600 MHz, CDCl$_3$) δ 4.11 (s, 2H), 3.44-3.39 (m, 2H), 3.33 (s, 3H), 1.86-1.71 (m, 5H), 1.66-1.54 (m, 1H), 1.03 (t, J=7.5 Hz, 3H); $^{13}$C NMR (150 MHz, CDCl$_3$) δ 173.85, 71.68, 68.28, 61.29, 58.13, 28.44, 24.81, 24.09, 8.23; HRMS (ESI-TOF) Calcd for C$_9$H$_{17}$O$_3$ [M+H]$^+$: 173.1178; found: 173.1189.

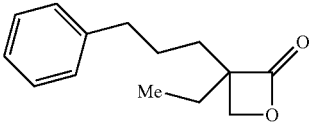 [SMILES: CCC1(CCCc2ccccc2)COC1=O]

Following General Procedure on 0.1 mmol scale. Purification by pTLC afforded the title compound (colorless oil, 12.8 mg, 59% yield). $^1$H NMR (600 MHz, CDCl$_3$) δ 7.33-7.27 (m, 2H), 7.23-7.18 (m, 1H), 7.18-7.13 (m, 2H), 4.08 (d, J=5.2 Hz, 1H), 4.06 (d, J=5.2 Hz, 1H), 2.72-2.62 (m, 2H), 1.86-1.69 (m, 5H), 1.69-1.61 (m, 1H), 0.99 (t, J=7.5 Hz, 3H); $^{13}$C NMR (150 MHz, CDCl$_3$) δ 174.37, 141.49, 128.59, 128.49, 126.20, 68.76, 62.11, 35.97, 31.80, 26.24, 25.47, 8.84; HRMS (ESI-TOF) Calcd for C$_{14}$H$_{19}$O$_2$ [M+H]$^+$: 219.1385; found: 219.1387.

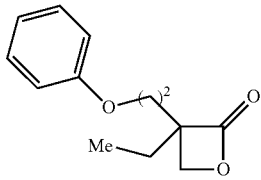

Following General Procedure on 0.1 mmol scale. Purification by pTLC afforded the title compound (colorless oil, 15.0 mg, 68% yield). $^1$H NMR (500 MHz, CDCl$_3$) δ 7.36-7.29 (m, 2H), 7.03-6.96 (m, 1H), 6.93-6.85 (m, 2H), 4.45 (d, J=5.3 Hz, 1H), 4.20 (d, J=5.3 Hz, 1H), 4.19-4.16 (m, 1H), 4.16-4.08 (m, 1H), 2.42-2.32 (m, 1H), 2.26-2.16 (m, 1H), 1.91-1.82 (m, 2H), 1.11 (t, J=7.5 Hz, 3H); $^{13}$C NMR (125 MHz, CDCl$_3$) δ 174.10, 158.39, 129.71, 121.36, 114.49, 69.72, 63.74, 60.35, 31.49, 25.37, 8.87.

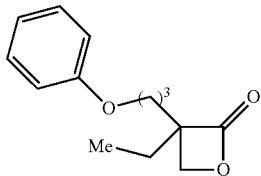

Following General Procedure on 0.1 mmol scale. Purification by pTLC afforded the title compound (colorless oil, 21.0 mg, 90% yield). $^1$H NMR (500 MHz, CDCl$_3$) δ 7.32-7.24 (m, 2H), 6.98-6.91 (m, 1H), 6.91-6.84 (m, 2H), 4.13 (s, 2H), 4.02-3.96 (m, 2H), 2.05-1.89 (m, 3H), 1.89-1.75 (m, 3H), 1.05 (t, J=7.5 Hz, 3H); $^{13}$C NMR (125 MHz, CDCl$_3$) δ 174.25, 158.82, 129.63, 120.98, 114.54, 68.92, 67.31, 61.86, 29.08, 25.38, 24.50, 8.83; HRMS (ESI-TOF) Calcd for C$_{14}$H$_{19}$O$_3$ [M+H]$^+$: 235.1334; found: 235.1336.

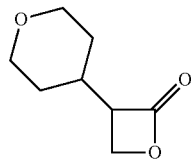 [SMILES: O=C1OCC1C1CCOCC1]

Following General Procedure on 0.1 mmol scale. Purification by dissolution with EA and saturated NaHCO$_3$ aqueous wash afforded the title compound (colorless oil, 8.0 mg, 51%). $^1$H NMR (600 MHz, CDCl$_3$) δ 4.33 (dd, J=6.4.5.4 Hz, 1H), 4.11 (dd, J=5.4, 4.6 Hz, 1H), 4.04-3.98 (m, 2H), 3.62 (ddd, J=8.5, 6.4, 4.6 Hz, 1H), 3.46-3.38 (m, 2H), 2.12-2.00 (m, 1H), 1.93-1.85 (m, 1H), 1.55-1.46 (m, 2H); $^{13}$C NMR (150 MHz, CDCl$_3$) δ 170.40, 67.47, 67.42, 62.77, 57.36, 34.55, 30.29, 30.22; HRMS (ESI-TOF) Calcd for C$_8$H$_{13}$O$_3$ [M+H]$^+$: 157.0865; found: 157.0852.

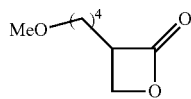

Following General Procedure on 0.1 mmol scale. Purification by dissolution with EA and saturated NaHCO$_3$ aqueous wash afforded the title compound (colorless oil, 13.0 mg, 82%). $^1$H NMR (600 MHz, CDCl$_3$) δ 4.37 (dd, J=6.3, 5.2 Hz, 1H), 4.05-4.00 (m, 1H), 3.75-3.68 (m, 1H), 3.39 (t, J=6.1 Hz, 2H), 3.33 (s, 3H), 1.95-1.85 (m, 1H), 1.83-1.76 (m, 1H), 1.65-1.52 (m, 3H), 1.51-1.43 (m, 1H); $^{13}$C NMR (150 MHz, CDCl$_3$) δ 171.85, 72.36, 65.11, 58.75, 52.17, 29.36, 28.09, 23.76.

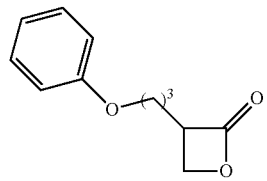

Following General Procedure on 0.1 mmol scale. Purification by pTLC afforded the title compound (colorless oil, 14.5 mg, 69%). $^1$H NMR (600 MHz, CDCl$_3$) δ 7.32-7.27 (m, 2H), 6.99-6.92 (m, 1H), 6.91-6.85 (m, 2H), 4.40 (dd, J=6.3, 5.3 Hz, 1H), 4.05 (dd, J=5.3, 4.5 Hz, 1H), 4.03-3.98 (m, 2H), 3.84-3.77 (m, 1H), 2.35 (t, J=7.5 Hz, 1H), 2.14-1.95 (m, 4H), 1.95-1.85 (m, 1H), 1.68-1.60 (m, 1H); $^{13}$C NMR (150 MHz, CDCl$_3$) δ 171.64, 158.78, 129.68, 121.06, 114.52, 66.92, 65.28, 51.96, 26.77, 25.38; HRMS (ESI-TOF) Calcd for C$_{12}$H$_{15}$O$_3$ [M+H]$^+$: 207.1021; found: 207.1023.

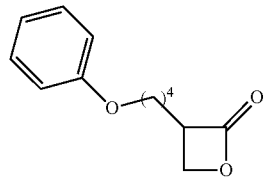

Following General Procedure on 0.1 mmol scale. Purification by pTLC afforded the title compound (colorless oil, 7.0 mg, 32%). $^1$H NMR (600 MHz, CDCl$_3$) δ 7.30-7.26 (m, 2H), 6.97-6.91 (m, 1H), 6.91-6.86 (m, 2H), 4.38 (dd, J=6.3, 5.2 Hz, 1H), 4.06-4.01 (m, 1H), 3.98 (t, J=6.2 Hz, 2H), 3.78-3.70 (m, 1H), 1.99-1.89 (m, 1H), 1.89-1.80 (m, 2H), 1.74-1.65 (m, 1H), 1.65-1.55 (m, 2H); $^{13}$C NMR (150 MHz, CDCl$_3$) δ 171.69, 158.99, 129.62, 120.87, 114.58, 67.32, 65.07, 52.18, 29.06, 28.06, 23.76; HRMS (ESI-TOF) Calcd for C$_{13}$H$_{17}$O$_3$ [M+H]$^+$: 221.1178; found: 221.1183.

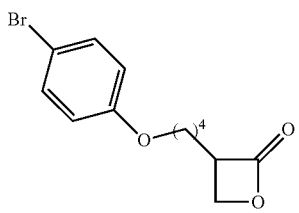

Following General Procedure on 0.1 mmol scale. Purification by pTLC afforded the title compound (colorless oil, 12.0 mg, 40%). $^1$H NMR (600 MHz, CDCl$_3$) δ 7.40-7.34 (m, 2H), 6.80-6.73 (m, 2H), 4.38 (dd, J=6.3, 5.2 Hz, 1H), 4.03 (dd, J=5.2, 4.5 Hz, 1H), 3.94 (t, J=6.2 Hz, 2H), 3.78-3.70 (m, 1H), 2.00-1.90 (m, 1H), 1.90-1.76 (m, 3H), 1.73-1.63 (m, 1H), 1.63-1.57 (m, 1H); $^{13}$C NMR (150 MHz, CDCl$_3$) δ 171.63, 158.12, 132.42, 116.38, 113.01, 67.71, 65.02, 52.14, 28.96, 28.04, 23.67; HRMS (ESI-TOF) Calcd for C$_{13}$H$_{16}$BrO$_3$ [M+H]$^+$: 299.0283; found: 299.0284.

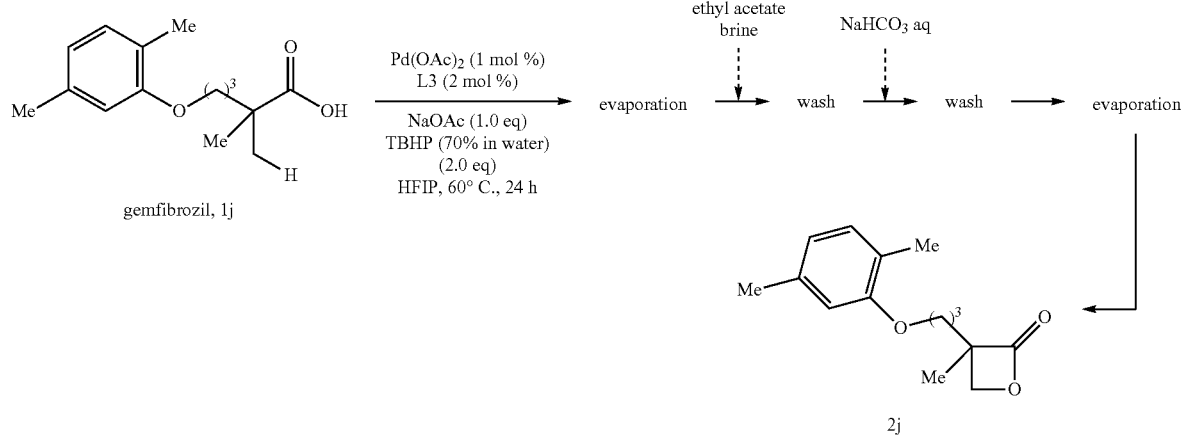

In a sealed tube, Pd(OAc)$_2$ (1.0 mol %, 2.6 mg), ligand L3 (2.0 mol %, 2.9 mg), NaOAc (1.0 eq, mg), and carboxylic acid 1 (4.0 mmol, 1.0 g) in order were weighed in air and placed with a magnetic stir bar. Then HFIP (40.0 mL) and TBHP (70% in water) (2.0 eq, 36 uL) were added. The reaction mixture was stirred at rt for 3 min, and then heated to 60° C. for 24 h (600 rpm). After being allowed to cool to room temperature, the mixture was concentrated in vacuo, and the resulting mixture purified by pTLC as the eluent or dissolution with EA and saturated NaHCO$_3$ aqueous wash.

General Procedure for Formal, β-C(sp$^3$)-H Functionalization

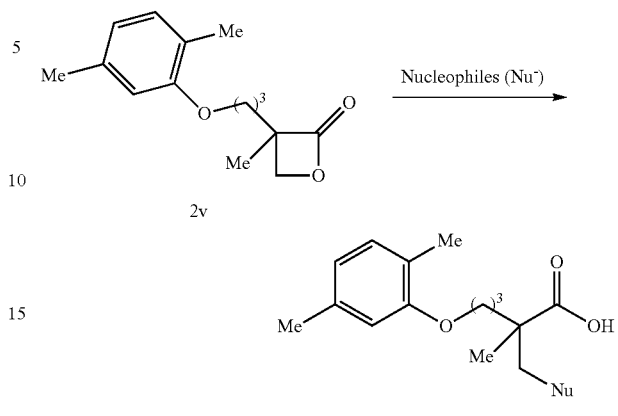

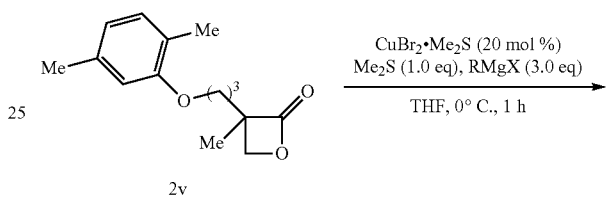

-continued

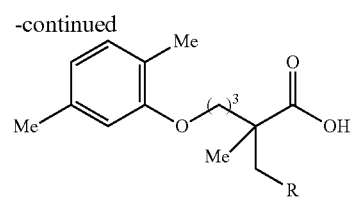

General Procedure A: In a culture tube, CuBr$_2$.Me$_2$S (20 mol %, 4.1 mg), β-lactone 2v (0.1 mmol, 24.8 mg), and MC₂S (1.0 eq, 7 uL) in order were added in air and placed with a magnetic stir bar. Then THF (1.0 mL) were added. The reaction mixture was stirred at rt for 3 min, and then Grignard reagent (3.0 eq) was added dropwise at 0° C. After being allowed to stir at 0° C. in 1 h, the mixture was quenched with saturated NH₄Cl. The result mixture was diluted with EA, washed with saturated NH₄Cl, and dried with MgSO₄. After being concentrated in vacuo, the resulting mixture was purified by pTLC using hexane/EA with AcOH (1%) if necessary as eluent.

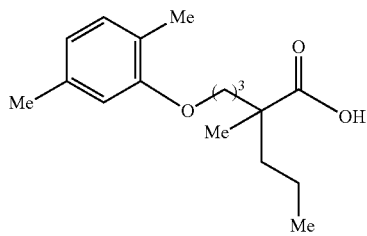

Following General Procedure A on 0.1 mmol scale. Purification by pTLC afforded the title compound (colorless oil, 26.0 mg, 93%). ¹H NMR (600 MHz, CDCl₃) δ 6.99 (d, J=7.5 Hz, 1H), 6.65 (dd, J=7.5, 1.5 Hz, 1H), 6.60 (d, J=1.5 Hz, 1H), 3.97-3.86 (m, 2H), 2.30 (s, 3H), 2.17 (s, 3H), 1.87-1.78 (m, 2H), 1.78-1.69 (m, 1H), 1.69-1.61 (m, 2H), 1.49 (ddd, J=13.4, 12.3, 4.6 Hz, 1H), 1.40-1.26 (m, 2H), 1.20 (s, 3H), 0.92 (t, J=7.3 Hz, 3H); ¹³C NMR (150 MHz, CDCl₃) δ 184.00, 157.07, 136.59, 130.43, 123.72, 120.82, 112.06, 68.06, 45.72, 41.45, 35.39, 24.88, 21.55, 21.38, 17.88, 15.90, 14.71; HRMS (ESI-TOF) Calcd for C₁₇H₂₆NaO₃ [M+Na]⁺: 301.1780; found: 301.1771.

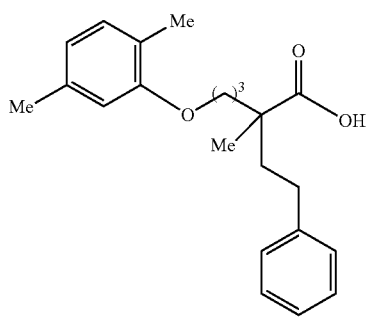

Following General Procedure A on 0.1 mmol scale. Purification by pTLC afforded the title compound (colorless oil, 28.0 mg, 82%). ¹H NMR (600 MHz, CDCl₃) δ 7.32-7.21 (m, 2H), 7.22-7.14 (m, 3H), 6.99 (d, J=7.5 Hz, 1H), 6.65 (d, J=7.5 Hz, 1H), 6.61 (s, 1H), 4.00-3.87 (m, 2H), 2.71-2.54 (m, 2H), 2.30 (s, 3H), 2.17 (s, 3H), 2.07-1.97 (m, 1H), 1.95-1.70 (m, 5H); ¹³C NMR (150 MHz, CDCl₃) δ 183.85, 157.02, 142.15, 136.59, 130.46, 128.54, 128.49, 126.04, 123.71, 120.87, 112.04, 67.92, 45.74, 40.99, 35.42, 31.19, 24.85, 21.55, 15.94 (1 carbon signal was not assigned due to overlaps);

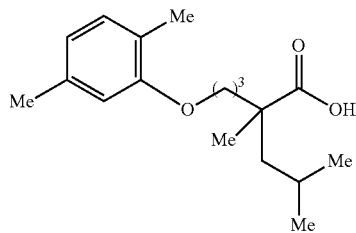

Following General Procedure A on 0.1 mmol scale. Purification by pTLC afforded the title compound (colorless oil, 23.0 mg, 79%). ¹H NMR (600 MHz, CDCl₃) δ 6.99 (d, J=7.5 Hz, 1H), 6.65 (dd, J=7.5, 1.5 Hz, 1H), 6.60 (d, J=1.5 Hz, 1H), 4.00-3.85 (m, 2H), 2.30 (s, 3H), 2.17 (s, 3H), 1.90-1.79 (m, 2H), 1.79-1.58 (m, 4H), 1.46 (dd, J=13.9, 5.4 Hz, 1H), 1.20 (s, 3H), 0.91 (d, J=6.6 Hz, 3H), 0.88 (d, J=6.6 Hz, 3H); ¹³C NMR (150 MHz, CDCl₃) δ 184.66, 157.08, 136.58, 130.43, 123.73, 120.82, 112.05, 68.04, 48.29, 45.25, 36.65, 24.98, 24.72, 24.55, 23.34, 21.54, 21.15, 15.90; HRMS (ESI-TOF) Calcd for C₁₈H₂₉O₃ [M+H]⁺: 293.2117; found: 293.2115.

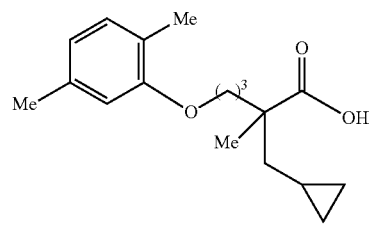

Following General Procedure A on 0.1 mmol scale. Purification by pTLC afforded the title compound (colorless oil, 22.0 mg, 76%). ¹H NMR (600 MHz, CDCl₃) δ 6.99 (d, J=7.5 Hz, 1H), 6.70-6.64 (m, 1H), 6.61 (d, J=1.5 Hz, 1H), 4.00-3.87 (m, 2H), 2.30 (s, 3H), 2.17 (s, 3H), 1.96-1.87 (m, 1H), 1.88-1.79 (m, 1H), 1.79-1.70 (m, 1H), 1.72-1.64 (m, 1H), 1.62 (dd, J=14.0, 6.9 Hz, 1H), 1.53-1.45 (m, 1H), 1.28 (s, 3H), 0.75-0.67 (m, 1H), 0.53-0.39 (m, 2H), 0.14-0.04 (m, 2H); ¹³C NMR (150 MHz, CDCl₃) δ 184.13, 157.08, 136.58, 130.42, 123.73, 120.82, 112.08, 68.09, 46.52, 44.22, 35.51, 24.97, 21.55, 21.42, 15.90, 6.77, 4.78, 4.36; HRMS (ESI-TOF) Calcd for C₁₈H₂₇O₃ [M+H]⁺: 291.1960; found: 291.1953.

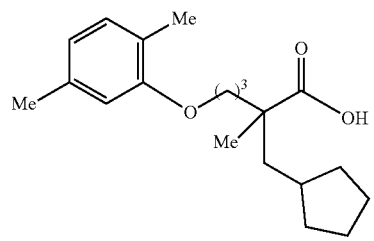

Following General Procedure A on 0.1 mmol scale. Purification by pTLC afforded the title compound (colorless oil, 21.0 mg, 66%). ¹H NMR (600 MHz, CDCl₃) δ 6.99 (d, J=7.5 Hz, 1H), 6.65 (d, J=7.5 Hz, 1H), 6.60 (s, 1H), 3.99-3.86 (m, 2H), 2.30 (s, 3H), 2.17 (s, 3H), 1.91-1.68 (m, 7H), 1.68-1.53 (m, 4H), 1.52-1.40 (m, 2H), 1.22 (s, 3H), 1.14-1.02 (m, 2H); ¹³C NMR (150 MHz, CDCl₃) δ 184.53, 157.08, 136.58, 130.42, 123.72, 120.81, 112.05, 68.07, 45.86, 45.76, 36.99, 36.23, 34.37, 33.65, 25.19, 24.98, 24.87, 21.55, 21.47, 15.91.

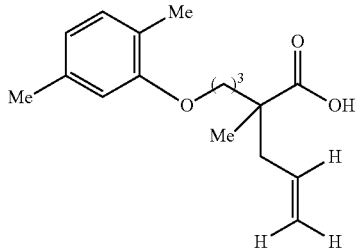

Following General Procedure A on 0.1 mmol scale. Purification by pTLC afforded the title compound (colorless oil, 25.0 mg, 91%). $^1$H NMR (600 MHz, CDCl$_3$) δ 7.00 (d, J=7.4 Hz, 1H), 6.65 (d, J=7.4 Hz. 1H), 6.60 (s, 1H), 5.83-5.72 (m, 1H), 5.15-5.10 (m, 1H), 5.09 (s, 1H), 3.96-3.88 (m, 2H), 2.44 (dd, J=13.8, 7.1 Hz, 1H), 2.34-2.25 (m, 4H), 2.17 (s, 3H), 1.88-1.71 (m, 3H), 1.71-1.63 (m, 1H), 1.21 (s, 3H); $^{13}$C NMR (150 MHz, CDCl$_3$) δ 183.29, 157.05, 136.59, 133.65, 130.44, 123.73, 120.85, 118.59, 112.04, 67.94, 43.03, 35.05, 24.88, 21.55, 21.49, 15.91 (1 carbon signal was not assigned due to overlaps); HRMS (ESI-TOF) Calcd for C$_{17}$H$_{24}$NaO$_3$ [M+Na]$^+$: 299.1623; found: 299.1613.

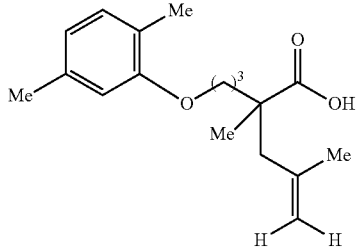

Following General Procedure A on 0.1 mmol scale. Purification by pTLC afforded the title compound (colorless oil, 23.5 mg, 81%). $^1$H NMR (600 MHz, CDCl$_3$) δ 7.00 (d, J=7.4 Hz, 1H), 6.65 (d, J=7.4 Hz, 1H), 6.60 (s, 1H), 4.85 (s, 1H), 4.72 (s, 1H), 3.98-3.87 (m, 2H), 2.54 (d, J=13.7 Hz, 1H), 2.30 (s, 3H), 2.23 (d, J=13.7 Hz, 1H), 2.17 (s, 3H), 1.96-1.81 (m, 2H), 1.77-1.74 (m. 1H), 1.72 (s, 3H), 1.67-1.58 (m, 1H), 1.20 (s, 3H); $^{13}$C NMR (150 MHz, CDCl$_3$) δ 183.81, 157.05, 141.99, 136.59, 130.44, 123.73, 120.85, 114.97, 112.05, 67.96, 47.58, 45.58, 36.40, 24.90, 23.83, 21.55, 21.01, 15.91; HRMS (ESI-TOF) Calcd for C$_{18}$H$_{27}$O$_3$ [M+H]$^+$: 291.1960. found: 291.1961.

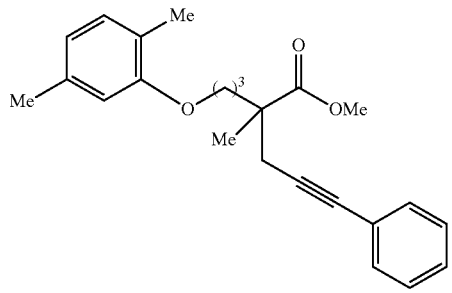

Following General Procedure on 0.1 mmol scale. Purification by pTLC afforded the title compound (colorless oil, 25.5 mg, 70%). $^1$H NMR (600 MHz, CDCl$_3$) δ 7.41-7.35 (m, 2H), 7.30-7.25 (m, 3H), 6.99 (d, J=7.4 Hz, 1H), 6.67 (d, J=7.4 Hz. 1H), 6.65-6.61 (m. 1H), 4.04 (d, J=8.7 Hz, 1H), 3.95 (d, J=8.7 Hz, 1H), 3.70 (s, 3H), 2.42 (t, J=7.0 Hz, 2H), 2.31 (s, 3H), 2.13 (s, 3H), 1.95 (td, J=12.8, 4.9 Hz, 1H), 1.80 (td, J=12.8, 4.6 Hz, 1H), 1.67-1.55 (m, 2H), 1.37 (s, 3H); $^{13}$C NMR (150 MHz, CDCl$_3$) δ 176.04, 156.79, 136.71, 131.69, 130.44, 128.33, 127.73, 124.01, 123.84, 121.12, 112.03, 89.67, 81.18, 72.60, 52.09, 47.13, 35.25, 24.04, 21.51, 20.40, 20.01, 15.82.

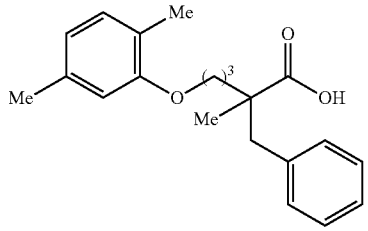

Following General Procedure A on 0.1 mmol scale. Purification by pTLC afforded the title compound (colorless oil, 20.0 mg, 61%). $^1$H NMR (600 MHz, CDCl$_3$) δ 7.31-7.26 (m, 2H), 7.26-7.19 (m, 2H), 7.20-7.14 (m, 1H), 7.00 (d, J=7.5 Hz, 1H), 6.66 (d, J=7.5 Hz, 1H), 6.61 (s, 1H), 4.03-3.83 (m, 2H), 3.06 (d, J=13.4 Hz, 1H), 2.82 (d, J=13.4 Hz, 1H), 2.31 (s, 3H), 2.17 (s, 3H), 1.99-1.76 (m, 3H), 1.65 (td, J=12.3, 4.1 Hz. 1H), 1.17 (s, 3H); $^{13}$C NMR (150 MHz, CDCl$_3$) δ 182.32, 157.04, 137.31, 136.62, 130.46, 130.40, 128.25, 126.78, 123.75, 120.88, 112.06, 67.94, 45.18, 35.49, 25.13, 21.56, 21.01, 15.94 (1 carbon signal was not assigned due to overlaps):

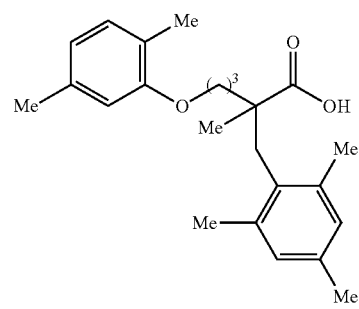

Following General Procedure A on 0.1 mmol scale. Purification by pTLC afforded the title compound (colorless oil, 25.0 mg, 68%). $^1$H NMR (600 MHz, CDCl$_3$) δ 7.00 (d, J=7.5 Hz, 1H). 6.82 (s, 2H), 6.66 (d, J=7.5 Hz. 1H), 6.61 (s, 1H), 4.02-3.85 (m, 2H), 3.20 (d, J=14.8 Hz, 1H), 2.99 (d, J=14.8 Hz, 1H), 2.30 (s, 3H), 2.28 (s, 6H), 2.23 (s, 3H), 2.17 (s, 3H), 2.15-2.06 (m, 1H), 1.91-1.81 (m, 1H), 1.78-1.61 (m, 2H), 1.11 (s, 3H); $^{13}$C NMR (150 MHz, CDCl$_3$) δ 183.67, 157.07, 137.86, 136.62, 135.75, 131.87, 130.46, 129.37, 123.75, 120.87, 112.10, 68.02, 47.32, 38.50, 37.07, 25.49, 21.55, 21.38, 20.90, 20.26, 15.91; HRMS (ESI-TOF) Calcd for C$_{24}$H$_{32}$NaO$_3$ [M+Na]$^+$: 391.2249; found: 391.2247.

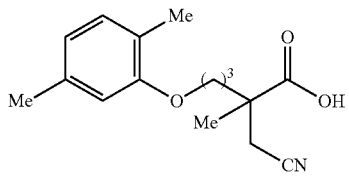

Following General Procedure on 0.1 mmol scale. Purification by pTLC afforded the title compound (colorless oil, 27.0 mg, 98%). $^1$H NMR (600 MHz, CDCl$_3$) δ 7.04-6.97 (m, 1H), 6.67 (dd, J=7.5, 1.5 Hz, 1H), 6.59 (d, J=1.5 Hz, 1H), 3.95 (t, J=6.0 Hz, 2H), 2.72 (d, J=16.8 Hz, 1H), 2.64 (d, J=16.8 Hz, 1H), 2.30 (s, 3H). 2.17 (s, 3H), 2.04-1.86 (m, 2H), 1.86-1.72 (m, 2H), 1.45 (s, 3H); $^{13}$C NMR (150 MHz, CDCl$_3$) δ 180.16, 156.75, 136.66, 130.54, 123.69, 121.12, 117.31, 112.01, 67.18, 34.90, 25.86, 24.91, 23.17, 21.53, 15.89 (1 carbon signal was not assigned due to overlaps); HRMS (ESI-TOF) Calcd for C$_{16}$H$_{22}$NO$_3$ [M+H]$^+$: 276.1600; found: 276.1603.

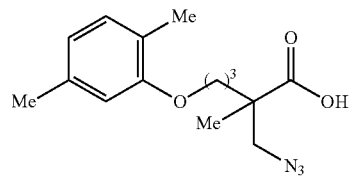

Following General Procedure on 0.1 mmol scale. Purification by pTLC afforded the title compound (colorless oil, 25.0 mg, 86%). $^1$H NMR (600 MHz, CDCl$_3$) δ 7.00 (d, J=7.5 Hz, 1H), 6.66 (d, J=7.5 Hz, 1H), 6.63-6.53 (m, 1H), 3.93 (t, J=5.5 Hz, 2H), 3.60 (d, J=12.1 Hz, 1H), 3.43 (d, J=12.1 Hz, 1H), 2.30 (s, 3H), 2.17 (s, 3H), 1.88-1.72 (m, 4H), 1.29 (s, 3H); $^{13}$C NMR (150 MHz, CDCl$_3$) δ 181.17, 156.90, 136.63, 130.49, 129.68, 123.72, 121.00, 112.06, 67.59, 57.85, 46.89, 33.16, 24.63, 21.54, 20.50, 15.88; HRMS (ESI-TOF) Calcd for C$_{15}$H$_{21}$N$_3$NaO$_3$ [M+Na]$^+$: 314.1481; found: 314.1477.

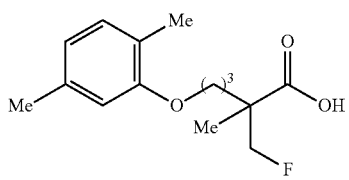

Following General Procedure on 0.1 mmol scale. Purification by pTLC afforded the title compound (colorless oil, 13.5 mg, 50%). $^1$H NMR (600 MHz, CDCl$_3$) δ 7.00 (d, J=7.3 Hz, 1H), 6.66 (d, J=7.3 Hz, 1H), 6.60 (s, 1H), 4.55 (dd, J=47.1, 9.0 Hz, 1H), 4.44 (dd, J=47.1, 9.0 Hz, 1H), 3.93 (t, J=5.5 Hz, 2H), 2.30 (s, 3H), 2.17 (s, 3H), 1.91-1.71 (m, 4H), 1.32 (s, 3H); $^{13}$C NMR (150 MHz, CDCl$_3$) δ 180.72, 156.93, 136.63, 130.49, 123.73, 120.99, 112.07, 87.11 (d, J=175.0 Hz), 67.66, 47.04 (d, J=18.3 Hz), 31.42 (d, J=4.8 Hz), 24.54, 21.53, 21.52, 19.11 (d, J=4.8 Hz), 15.87; HRMS (ESI-TOF) Calcd for C$_{15}$H$_{21}$FNaO$_3$ [M+Na]$^+$: 291.1372; found: 291.1363.

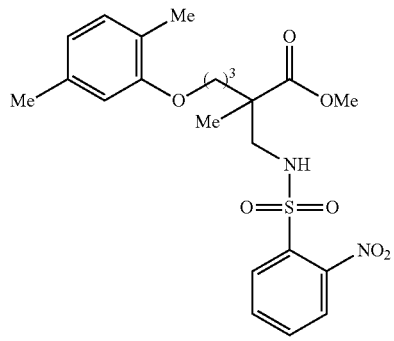

$^1$H NMR (600 MHz, CDCl$_3$) δ 8.16-8.04 (m, 1H), 7.90-7.79 (m, 1H), 7.79-7.66 (m, 2H), 6.99 (d, J=7.5 Hz, 1H), 6.66 (d, J=7.5 Hz, 1H), 6.57 (s, 1H), 5.98 (t, J=6.7 Hz, 1H), 3.95-3.82 (m, 2H), 3.70 (s, 3H), 3.27 (dd, J=12.6, 6.5 Hz, 1H), 3.10 (dd, J=12.6, 7.1 Hz, 1H), 2.30 (s, 3H), 2.15 (s, 3H), 1.85-1.69 (m, 4H), 1.28 (s, 3H); $^{13}$C NMR (150 MHz, CDCl$_3$) δ 176.34, 156.82, 148.26, 136.61, 133.70, 132.89, 131.02, 130.43, 125.53, 123.58, 120.94, 111.99, 67.47, 52.44, 49.66, 46.34, 33.45, 24.40, 21.50, 20.99, 15.86 (1 carbon signal was not assigned due to overlaps); HRMS (ESI-TOF) Calcd for C$_{22}$H$_{29}$N$_2$O$_7$S [M+H]$^+$: 465.1695; found: 465.1695.

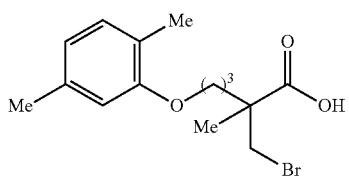

Following General Procedure on 0.1 mmol scale. Purification by pTLC afforded the title compound (colorless oil, 30.0 mg, 92%). $^1$H NMR (600 MHz, CDCl$_3$) δ 7.00 (d. J=7.4 Hz, 1H), 6.72-6.64 (m, 1H), 6.60 (d, J=1.6 Hz, 1H), 3.94 (t, J=5.8 Hz, 2H), 3.65 (d, J=10.2 Hz, 1H), 3.53 (d, J=10.2 Hz, 1H), 2.30 (s, 3H), 2.17 (s, 3H), 2.02-1.90 (m, 1H), 1.90-1.72 (m, 3H), 1.39 (s, 3H); $^{13}$C NMR (150 MHz, CDCl$_3$) δ 179.34, 156.31, 136.03, 129.89, 123.11, 120.38, 111.43, 66.91, 38.82, 33.46, 24.27, 20.96, 20.94, 15.30 (1 carbon signal was not assigned due to overlaps); HRMS (ESI-TOF) Calcd for C$_{15}$H$_{21}$BrNaO$_3$ [M+Na]$^+$: 351.0572; found: 351.0565.

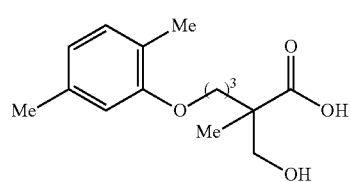

Following General Procedure on 0.1 mmol scale. Purification by pTLC afforded the title compound (colorless oil, 25.5 mg, 95%). $^1$H NMR (600 MHz, CDCl$_3$) δ 7.00 (d, J=7.5 Hz, 1H), 6.66 (dd, J=7.5, 1.4 Hz, 1H), 6.60 (d, J=1.4 Hz, 1H), 3.99-3.87 (m, 2H), 3.78 (d, J=11.3 Hz, 1H), 3.61 (d, J=11.3 Hz, 1H), 2.30 (s, 3H), 2.17 (s, 3H), 1.89-1.71 (m, 4H), 1.26 (s, 3H); $^{13}$C NMR (150 MHz, CDCl$_3$) δ 182.50, 156.96, 136.63, 130.48, 123.72, 120.98, 112.14, 68.04, 67.89, 32.30, 24.55, 21.54, 19.60, 15.90 (1 carbon signal was not assigned due to overlaps); HRMS (ESI-TOF) Calcd for $C_{15}H_{23}O_4$ [M+H]$^+$: 267.1596; found: 267.1596.

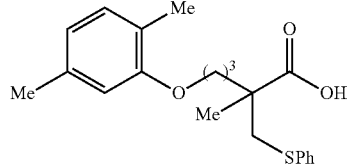

Following General Procedure on 0.1 mmol scale. Purification by pTLC afforded the title compound (colorless oil, 33.0 mg, 92%). $^1$H NMR (600 MHz, CDCl$_3$) δ 7.42-7.37 (m, 2H), 7.26-7.22 (m, 2H), 7.17 (t, J=7.3 Hz, 1H), 6.99 (d, J=7.4 Hz, 1H), 6.65 (d, J=7.4 Hz, 1H). 6.58 (s, 1H), 3.94-3.84 (m, 2H), 3.30 (d, J=12.7 Hz, 1H), 3.19 (d, J=12.7 Hz, 1H), 2.29 (s, 3H), 2.17 (s, 3H), 1.93 (dt, J=11.4, 6.6 Hz, 1H), 1.88-1.70 (m, 3H), 1.33 (s, 3H); $^{13}$C NMR (150 MHz, CDCl$_3$) δ 182.00, 156.97, 136.89, 136.58, 130.45, 130.36, 129.05, 126.57, 123.72, 120.90, 112.05, 67.71, 47.21, 43.06, 34.75, 24.88, 21.82, 21.54, 15.93; HRMS (ESI-TOF) Calcd for $C_{21}H_{26}NaO_3S$ [M+Na]$^+$: 381.1500; found: 381.1494.

Enumerated references cited in the examples section above are as follows:

1. Katritzky, A. R.; Xu, Y. J.; He, H. Y.; Mehta, S. *J. Org. Chem.* 2001, 66, 5590.
2. Adams, H.; Anderson, J. C.; Cubbon, R.; James, D. S.; Mathias, J. P. *J. Org. Chem.* 1999, 64, 8256.
3. M. Kawashima, T. Sato, T. Fujisawa, A facile method for synthesis of three carbon-homologated carboxylic acid by regioselective ring-opening of β-propiolactones with organocopper reagents. *Tetrahedron* 45, 403-412 (1989).
4. N. D. Smith, A. M. Wohlrab, M. Goodman, Enantiocontrolled synthesis of α-methyl amino acids via Bn$_2$N-α-methylserine-β-lactone. *Org. Lett.* 7, 255-258 (2005).
5. L. D. Arnold, T. H. Kalantar, J. C. Vederas, Conversion of serine to stereochemically pure β-substituted α-amino acids via β-Lactones. *J. Am. Chem. Soc.* 107, 7105-7109 (1985).
6. M. Shinoda, K. Iseki. T. Oguri, Y. Hayasi, S. Yamada, M. Shibasaki, A convenient synthesis of β-alkynylpropionic acids from β-propiolactones. Synthesis of 4,4,5,5-tetradehydro-9(O)-methano-Δ$^{6(9\alpha)}$-PGI$_1$. *Tetrahedron Let.* 27, 87-90 (1986).

All patent documents and publications cited in this disclosure are incorporated herein by reference as if fully set forth.

We claim:

1. A method of forming a beta-lactone of formula (2):

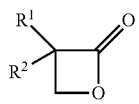 (2)

from a carboxylic acid having a beta-carbon with a hydrogen atom disposed thereon, comprising contacting a carboxylic acid of formula (1):

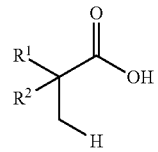 (1)

wherein

R$^1$ and R$^2$ are each independently H or alkyl, provided at least one of R$^1$ and R$^2$ is alkyl, wherein the alkyl is unsubstituted or is substituted with halo, oxo, dialkylphosphono, cycloalkyl, alkoxy, aryloxy, benzyloxy, heterocyclyl, aryl, or heteroaryl;

and an effective amount of a palladium(II) catalyst in the presence of an effective amount of an N-protected aminoacid ligand, and t-butylhydroperoxide in a solvent comprising hexafluoroisopropanol (HFIP), at about 60° C., to provide the beta-lactone of formula (2).

2. The method according to claim 1, further comprising contacting the beta-lactone of formula (2):

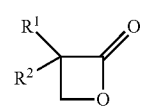 (2)

with a nucleophile (Nu$^-$) to provide a beta-functionalized carboxylic acid of formula (3):

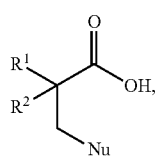 (3)

wherein Nu is selected from the group consisting of C(sp$^3$), C(sp$^2$), CN, N$_3$, 2-nitrophenylsulfonamido, OH, F, Br, and SPh.

3. The method according to claim 1 or 2, wherein the palladium(II) catalyst contains at least one palladium-chlorine bond.

4. The method according to claim 1 or 2, wherein the palladium(II) catalyst is Pd(CH$_3$CN)$_2$Cl$_2$ or Pd(OAc)$_2$.

5. The method according to claim 1, wherein the N-protected aminoacid ligand is one selected from the group consisting of L1-L6:

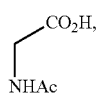 L1

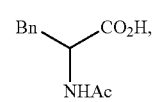 L2

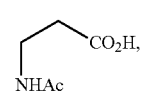 L3

-continued
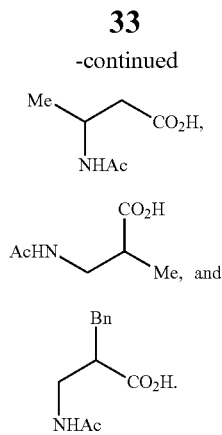
6. The method according to claim 1, wherein the N-protected aminoacid ligand is L5:
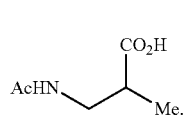
7. The method according to claim 1, wherein the beta-lactone of formula (2) is one selected from the following table:
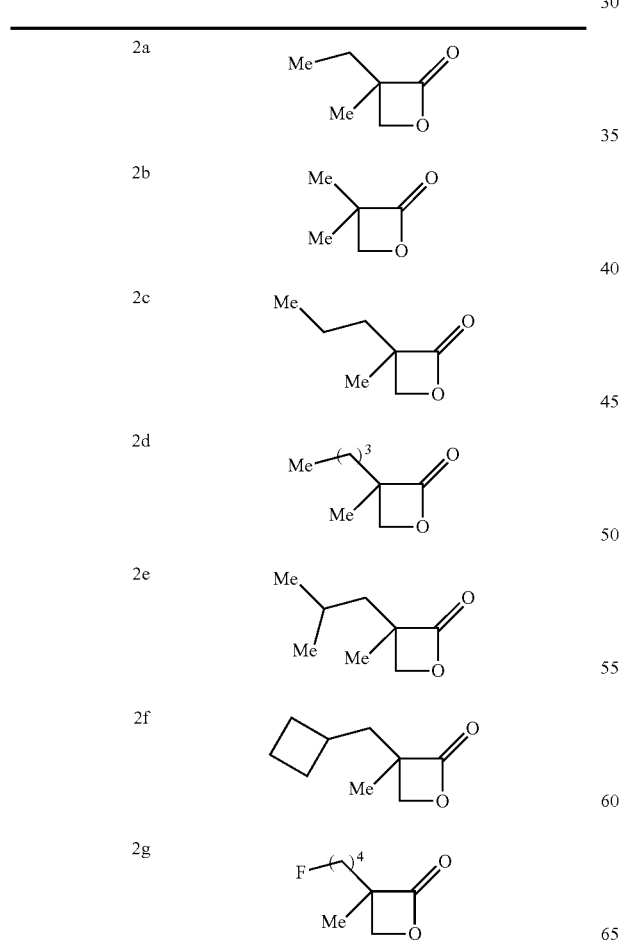
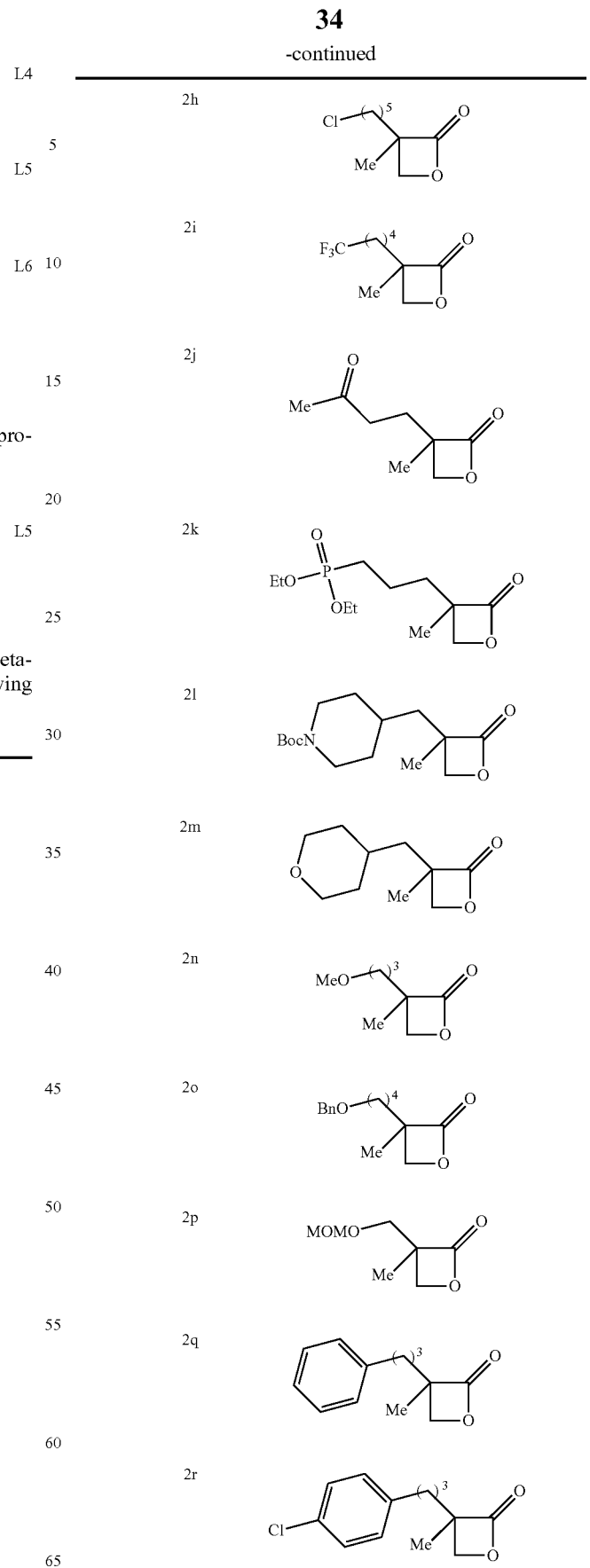

-continued
2s 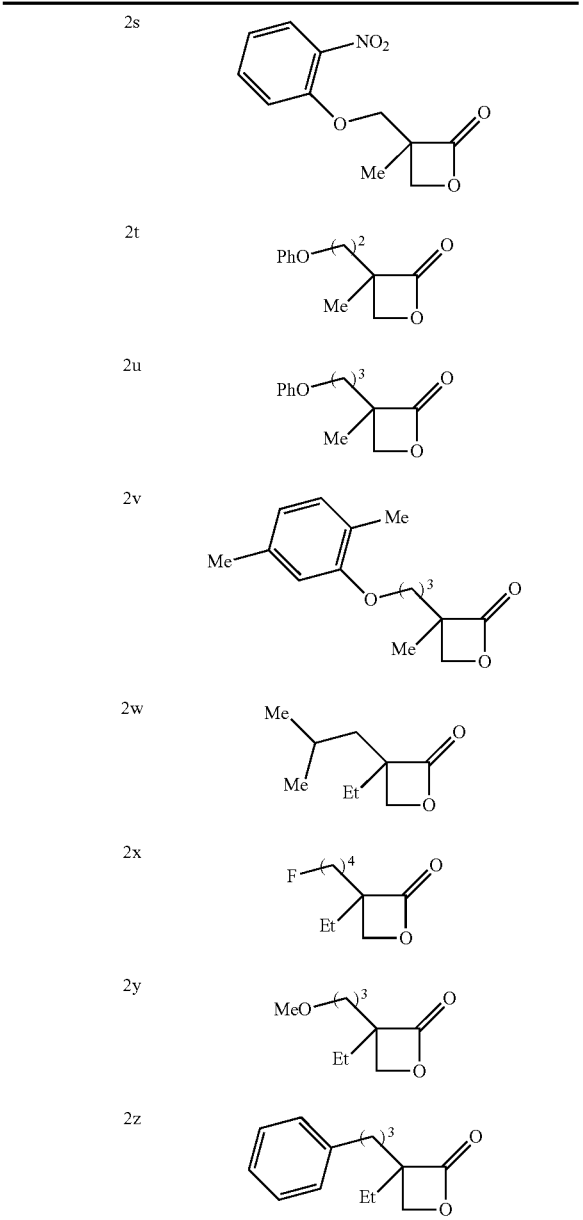
2t
2u
2v
2w
2x
2y
2z
-continued
2aa 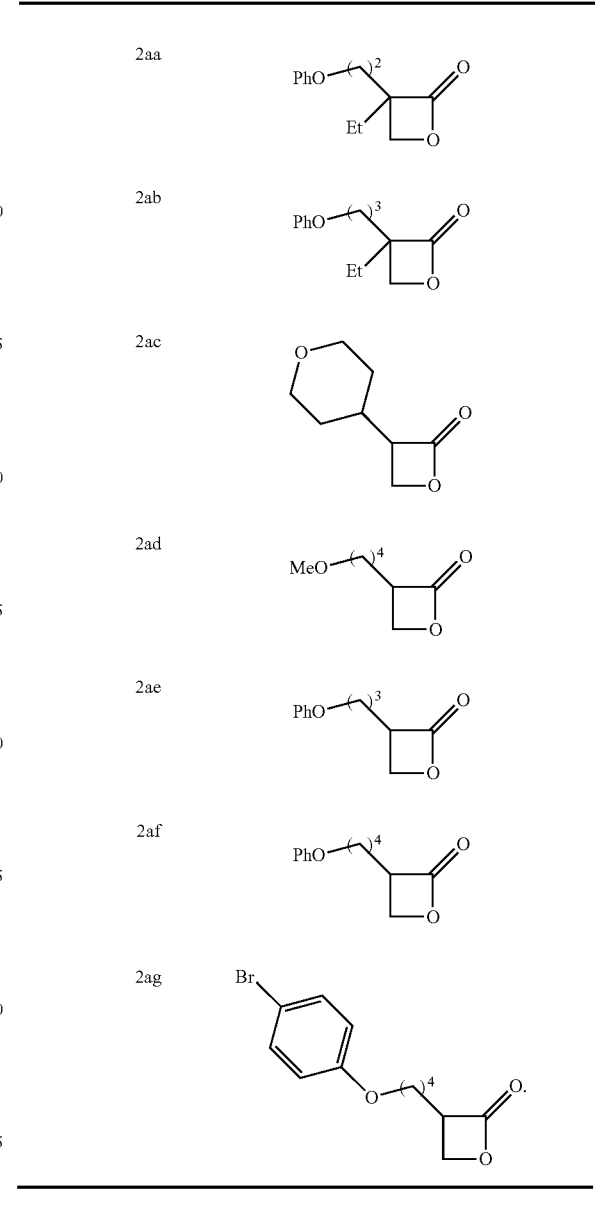
2ab
2ac
2ad
2ae
2af
2ag
* * * * *